United States Patent
Higgins

(10) Patent No.: US 10,486,158 B2
(45) Date of Patent: Nov. 26, 2019

(54) ENCLOSING HOLDER FOR A SAMPLE CONTAINER

(71) Applicant: Exact Sciences Corporation, Madison, WI (US)

(72) Inventor: Timothy E. Higgins, Madison, WI (US)

(73) Assignee: EXACT SCIENCES CORPORATION, Madison, WI (US)

( * ) Notice: Subject to any disclaimer, the term of this patent is extended or adjusted under 35 U.S.C. 154(b) by 0 days.

(21) Appl. No.: 15/050,026

(22) Filed: Feb. 22, 2016

(65) Prior Publication Data

US 2017/0239651 A1    Aug. 24, 2017

(51) Int. Cl.
*B01L 9/00* (2006.01)
*B01L 3/00* (2006.01)
*A61B 10/00* (2006.01)

(52) U.S. Cl.
CPC .......... *B01L 3/508* (2013.01); *A61B 10/0038* (2013.01); *B01L 9/00* (2013.01); *B01L 2200/02* (2013.01); *B01L 2200/0689* (2013.01); *B01L 2200/087* (2013.01); *B01L 2200/185* (2013.01); *B01L 2300/043* (2013.01)

(58) Field of Classification Search
CPC .......... B01L 2300/043; B01L 2200/04; B01L 2200/0647
USPC .................................... 422/561, 560
See application file for complete search history.

(56) References Cited

U.S. PATENT DOCUMENTS

2011/0030134 A1*  2/2011  Dubiel .................. A47K 11/06
                                                          4/483

FOREIGN PATENT DOCUMENTS

WO         2015/031832         3/2015

\* cited by examiner

*Primary Examiner* — Natalia Levkovich
(74) *Attorney, Agent, or Firm* — Casimir Jones, S.C.; Mary Ann D. Brow

(57) ABSTRACT

Provided herein is technology relating to processing samples and particularly, but not exclusively, to technology for containing and processing a stool specimen. The technology provides an enclosing holder for securing a sample container in a leak-proof manner e.g., during mechanical shaking.

15 Claims, 22 Drawing Sheets

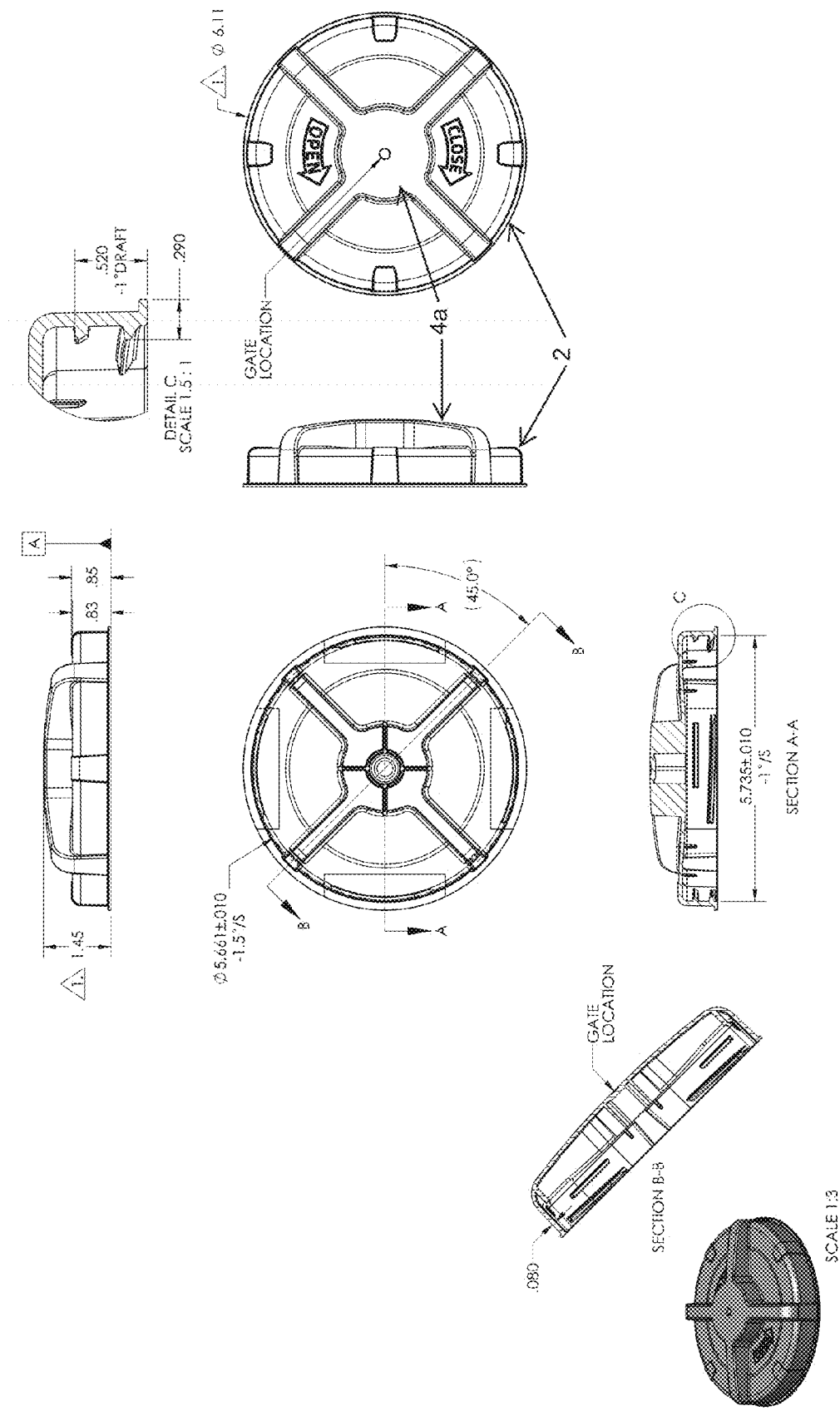

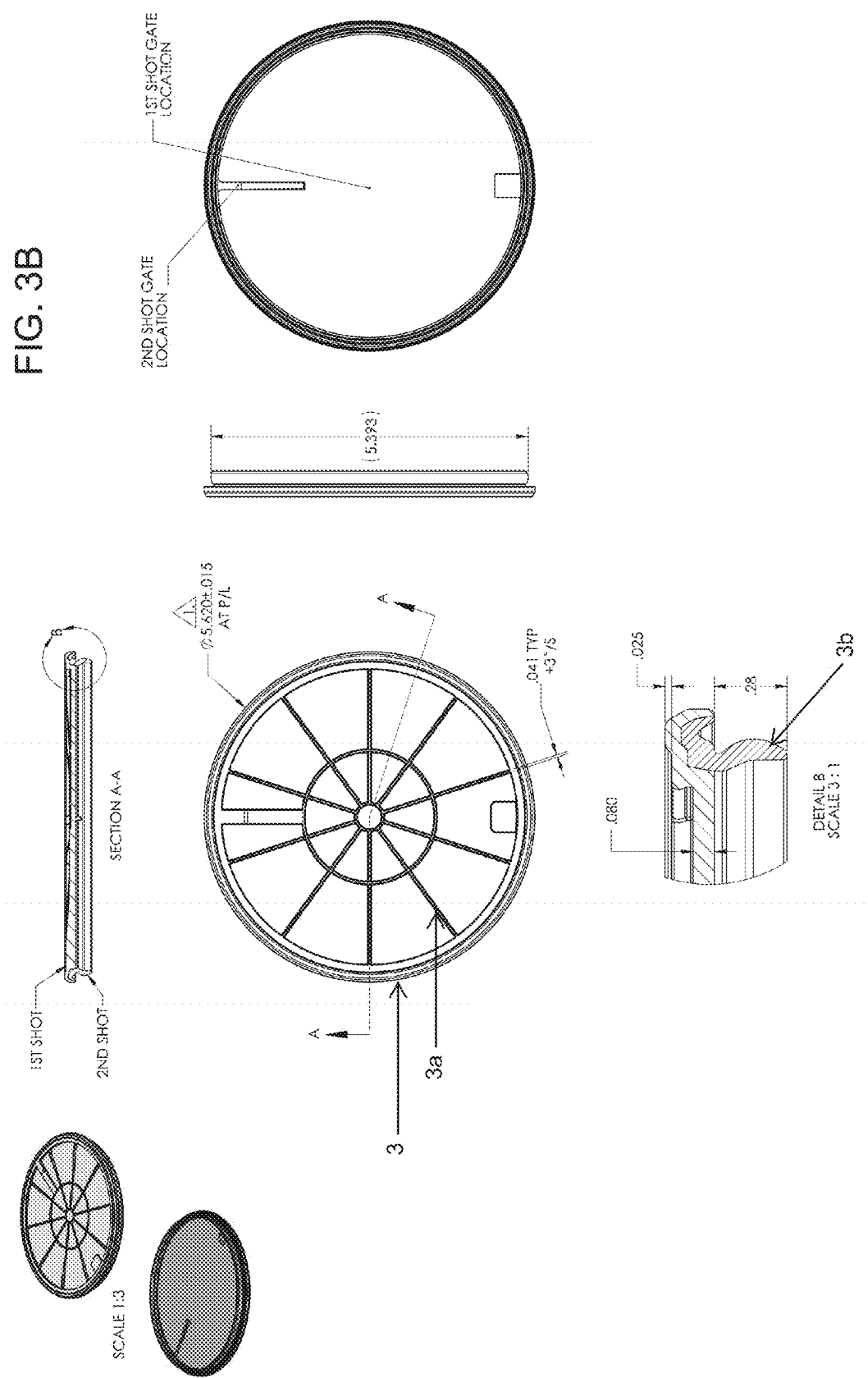

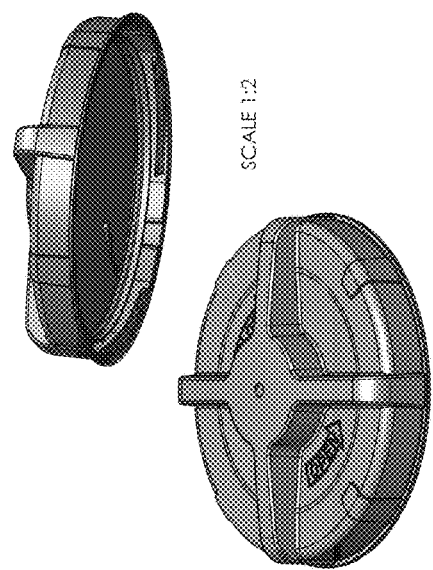
FIG. 3C
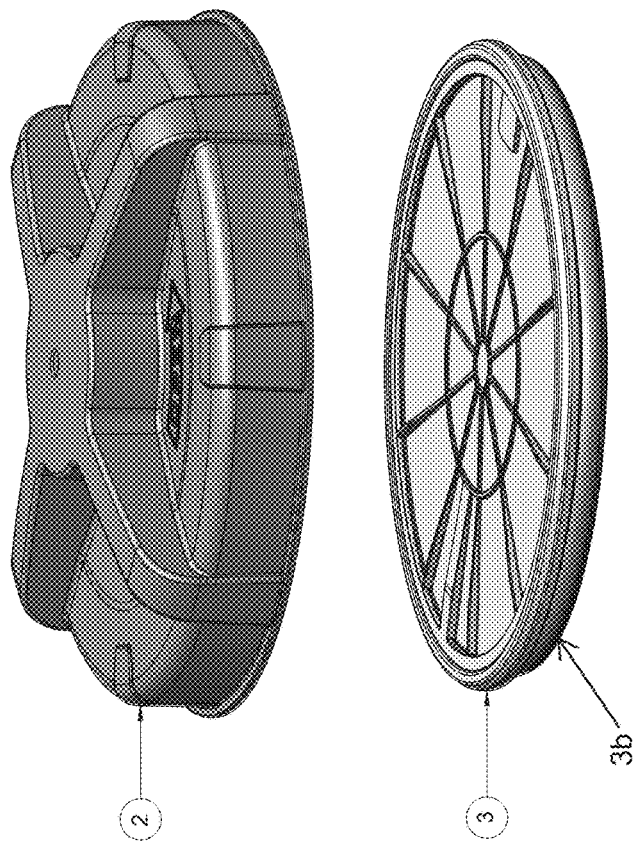

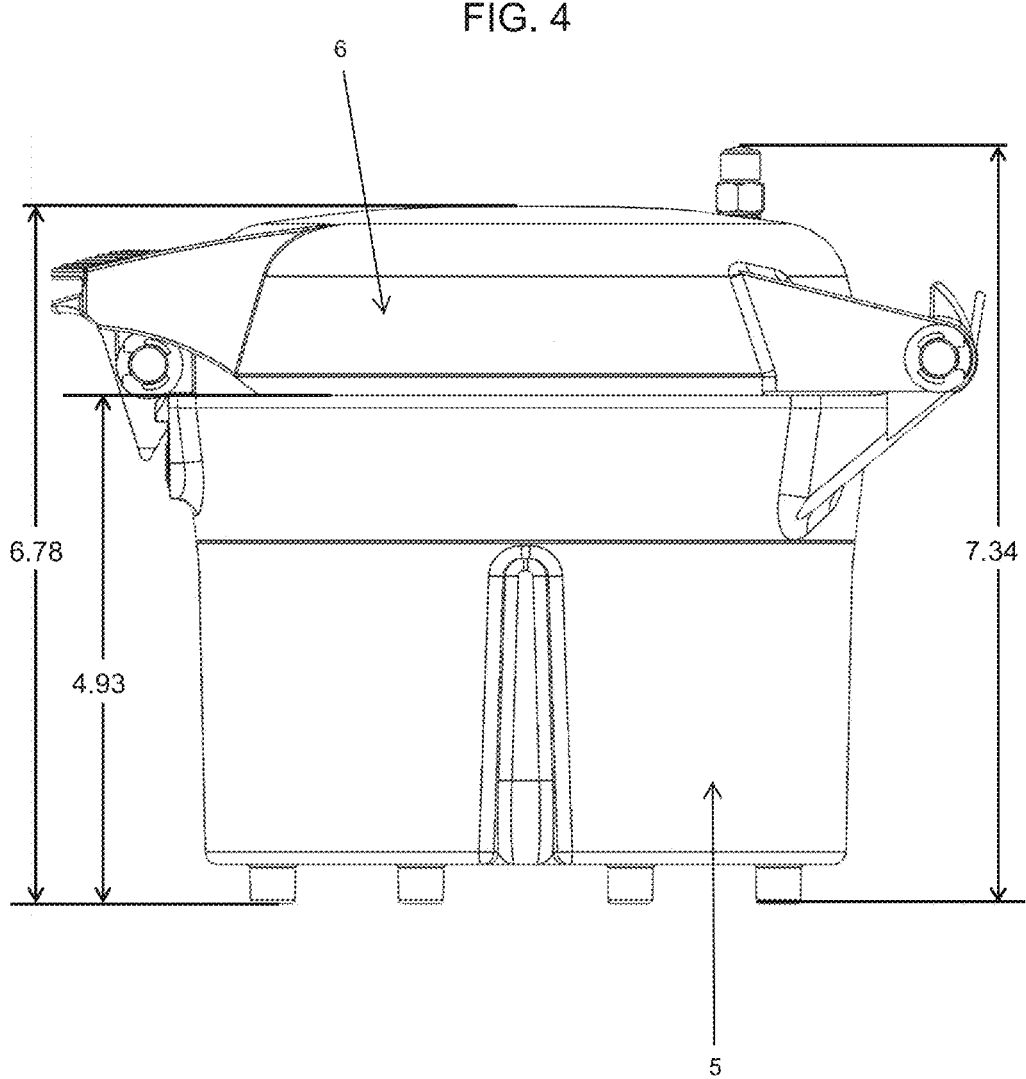

ENCLOSING HOLDER FOR A SAMPLE CONTAINER

FIELD OF INVENTION

Provided herein is technology relating to processing samples and particularly, but not exclusively, to technology for containing and processing a stool specimen.

BACKGROUND

In the medical clinic, laboratory examination of fecal samples is an important component of some diagnoses. In these cases, stool specimens are taken from a patient and examined for conditions relative to the ailment of the patient. As specific examples, physicians and clinicians often test stool samples as a component of testing for colon or rectal cancer or to identify bacteria or viruses that may be involved in an infection. Additionally, some diagnostics require isolating and assaying nucleic acids, proteins, fats, or other analytes present in a stool sample. Consequently, acquiring a specimen for testing (e.g., a stool specimen) is the first step in sample processing for many tests (e.g., the medical diagnostic analysis of feces). For samples collected by the patient, e.g., in their home, a container holding the collected sample must be suitable not only for storage of the sample until it is received in the lab, but also for transport and/or shipping of the sample to the lab where it will be examined.

Acquiring the stool specimen presents several challenges relating to, e.g., providing containers of sufficient size to receive and contain an entire sample, wherein the container is configured for handling and use by patients with different sizes of hands (e.g., small to large) and with varying degrees of hand strength, upper body strength, and/or fine motor skill and visual acuity. Patients over the age of about 50 years are particularly likely to be subject to screening methods requiring collection of stool specimens, and are also more likely have impairments in both hand usage (e.g., due to arthritis) and vision (e.g., age-related presbyopia, cataracts, macular degeneration). The likelihood of such impairments increases in older populations, e.g., in populations of geriatric patients.

Ergonomic sample containers are configured to allow for the comfortable acquisition of a stool specimen, are easy to use for the subjects providing stool specimens, and include features ensuring proper sealing, e.g., to prevent leakage during handling or shipping. However, transfer of samples prior to processing may increase risks of sample contamination. Thus, it is desirable to process samples directly in the containers used for collection.

SUMMARY

Provided herein is an enclosing holder for a sample container used for collection, containment, shipping, and/or mixing of a stool sample, comprising certain features designed for ease of use by a human subject. The enclosing holder is configured to contain and support a container, e.g., an ergonomic sample container comprising a stool, during further processing, and to reinforce the sealing of the container e.g., during shaking, rotating, gyroscopic mixing, or other mixing agitation.

Examples of ergonomic containers for collection and processing of stool samples are provided, e.g., in International Patent Publication WO 2015/031832, which is incorporated herein by reference in its entirety for all purposes. It is contemplated that embodiments of the enclosing holder find use with the ergonomic sample containers, kits, and methods described therein.

The technology herein provides a system wherein a sealed container as described above, received from a user, is moved directly to a processing step, such as homogenization or dispersal of the sample through agitation of the container using a mechanical shaker. The forces applied to a collection container during a mixing process may be substantial, and may further increase risk of leakage from a poorly or improperly sealed collection vessel.

For standard mechanical shakers (e.g., paint shakers, gyroscopic shakers, etc.), users typically employ containers having particularly secure seals (e.g., the friction seals on standard paint cans) that usually must be opened using a device (e.g., a paint can-opening tool or a pry bar). Even containers having such strong friction seals typically must also be clamped to secure the seal during shaking.

In a clinical laboratory setting, it is highly desirable for a sample container to have a lid that requires neither tools nor particular physical strength to open after sample collection and/or processing. An easily removable lid, however, presents a greater risk of leakage, especially during mechanical shaking. The leakage of even small amounts of a stool sample from a container during mixing is highly problematic. Leakage of medical samples not only poses a health and safety hazards to laboratory workers, it also increases risk of cross-contamination between patient samples, potentially compromising laboratory results.

The technology provides an enclosing holder for a sample container, e.g., an ergonomic sample container, the enclosing holder comprising a holder base and a holder top. In preferred embodiments, the holder base and the holder top are flexibly joined, e.g. with a hinge, and they comprise mated latching features such that the enclosing holder can be secured in a closed and sealed configuration. By way of example, in some embodiments a holder base comprises a first latching engagement feature (e.g., a catch) that is configured to engage a mated latching engagement feature (e.g., a latch) on a holder top. In preferred embodiments the enclosing holder is configured to be opened and closed with ease, e.g., using a single hand.

In some embodiments, the holder base and/or the holder top of the enclosing holder comprise sample container engagement features, e.g., guides or forms that are fitted to features on the outside of the container. In preferred embodiments, the sample engagement features aid in proper positioning of a sample container within the enclosing holder, and/or restrict or eliminate movement of the sample container within the enclosing holder, e.g., during mechanical shaking. In particularly preferred embodiments, sample engagement features within the enclosing holder serve to ensure that the sample container within remains sealed, e.g., by restricting or preventing movement of a sample container lid with respect to the sample container bucket. For example, for a sample container that is closed by screwing a threaded lid onto a bucket having mated threads, the enclosing holder may comprise sample engagement features that prevent the lid from rotating with respect to the bucket in a manner that would unscrew or loosen the lid. In some embodiments the holder top comprises a compression spring that exerts downward pressure on the lid of the sample container.

In some embodiments, sample container engagement features of the enclosing holder are integrated with the bodies of the base and/or top of the enclosing holder. In preferred embodiments, sample container engagement features of the enclosing holder are integrated with the bodies of both the base and top of the enclosing holder. In particularly preferred embodiments, the sample container engagement features are configured to engage an ergonomic sample container as shown in FIG. 3. In some embodiments, the sample container engagement features of the holder base engage with features of the sample container bucket and the sample container engagement features of the holder top engage with features of the sample container lid.

The technology herein further provides an enclosing holder comprising integrated hinges and/or handles. For example, in some embodiments, the holder base comprises a first integrated hinge portion and the holder top comprises a second, mated integrated hinge portion, and the holder base and holder top are flexibly connected at the hinge portions, e.g., with a hinge pin, such as a removable shoulder bolt. In preferred embodiments, the hinge comprises hinge stops to limit the range in which the holder top can be opened with respect to the holder base.

In some embodiments, the enclosing holder comprises a feature that will cause the holder to move to or stay in an open position when the top is not latched in a closed position. For example, in some embodiments, the enclosing holder comprises a spring, e.g., one or more torsion springs at the hinge, that will open the top when the latching engagement features are disengaged.

In preferred embodiments, an enclosing holder of the technology is configured to be closed and/or opened with one hand, e.g., so that a worker does not need to have two free hands to operate the enclosing holder. In particularly preferred embodiments, the enclosing holder can be both closed and opened with one hand. For example, in the embodiment diagrammed in FIG. 13A, when a sealed sample container is placed in the base of an open enclosing holder, the top is simply swung down into place and pressed to engage the latching mechanism, thereby sealing the sample container within the enclosing holder, with an O-ring providing the enclosing holder with a leak-proof seal. Opening the enclosing holder, as depicted in the panels of FIG. 13B, requires only upward pressure on a latch release on the underside of the handle. Upon disengagement of the latch, torsion springs open the top so that the sample container may be removed from the enclosing holder. In preferred embodiments, the handle of the enclosing holder is an integrated handle with respect to said holder top.

An enclosing holder of the technology is configured for use in a mechanical shaker e.g., a paint shaker, gyroscopic shaker, etc. In some embodiments, the enclosing holder is clamped to a shaker. In preferred embodiments, the enclosing holder is rigidly mounted, e.g., with screws or bolts, to a platform or hub that is attached to the shaker. In preferred embodiments, the enclosing holder comprises holes, e.g., threaded holes in the bottom of the base, whereby screws may be used to mount the enclosing holder to the mechanical shaker. In some embodiments, mounting holes are provided on the bottom of the holder base. In some embodiments, the mounting holes are provided in feet or legs that extend, for example, from a bottom surface of the holder base. The technology is not limited to any particular number of mounting holes, e.g., the holder base may comprise 1, 2, 3, 4, 5, 6, 7, 8, etc. mounting holes. The enclosing holder is not limited to one particular configuration for securing to a shaker, and need not have threaded holes. For example, in some embodiments, the holder comprises pegs, e.g., externally threaded feet or legs, that are secured to the shaker, for example, using bolts.

In some embodiments, the bodies of the holder base and/or said holder top, e.g., the principal components excluding non-integrated parts, are composed primarily or entirely of cast metal. In preferred embodiments, the cast metal is cast aluminum. In embodiments comprising integrated sample container engagement features, in preferred embodiments the integrated engagement features are directly cast as parts of the holder base and/or holder top.

In some embodiments, the technology provided an enclosing holder for a sealed ergonomic sample container for a stool specimen, wherein the ergonomic sample container can be sealed by hand by screwing a lid onto a bucket, and can be opened by hand by unscrewing the lid from the bucket, the enclosing holder comprising a holder top and a holder base, wherein, when a sealed ergonomic sample container is in the holder base, the enclosing holder can be closed and a latch engaged using one hand, and, when the enclosing holder is closed, the latch can be disengaged and the enclosing holder can be opened using one hand. Further, the enclosing holder is removably mountable to a mechanical shaker. In preferred embodiments, the holder top and the holder base comprise mated integrated hinge portions, and in particularly preferred embodiments, the holder further comprises a spring configured to move the holder top to an open position when the latch is disengaged.

In some embodiments the technology provides a system comprising an enclosing holder and an ergonomic sample holder, as described above, and in certain preferred embodiments, the system further comprises a stool homogenization solution. For example, in some embodiments, the stool homogenization solution of the system comprises a salt and a preservative or a stabilizing agent. In particularly preferred embodiments, the ergonomic sample container is sealed and contains the stool homogenization solution and a stool specimen, and the enclosing sample holder encloses the ergonomic sample container in a leak-proof manner.

BRIEF DESCRIPTION OF THE DRAWINGS

These and other features, aspects, and advantages of the present technology will become better understood with regard to the following drawings:

FIGS. 3A-3D show views of an embodiment of the device. FIG. 3A shows drawings of different views of a lid (2); FIG. 3B shows drawings of different views of a floating plate seal (3); FIG. 3C shows drawings of a lid (2) and a floating plate seal (3), both separately and as an assembly with the seal inside the lid; and FIG. 3D shows drawings of different views of a bucket (1).

FIGS. 4-11 show views of an embodiment of an enclosing holder for an ergonomic stool specimen container as shown in FIGS. 3A-3D.

FIG. 4 is a left side elevational view showing an embodiment of an enclosing holder comprising holder base (5) and holder top (6). Dimensions of the exemplary embodiment are shown in inches.

FIG. 5 is a front elevational view of the embodiment of an enclosing holder shown in FIG. 4, showing latch (11) with latch release (11*a*) on holder top (6) and catch (13) on holder base (6).

FIG. 6 is a right side elevational view of the embodiment of an enclosing holder shown in FIG. 4, showing the integrated hinge portions (8, 10) on the holder top (6) and base (5), respectively. The holder top (6) comprises a Schrader valve (14) and an integrated handle (7) and a latch (11). Holder base (5) comprises a plurality of feet (20) and catch (13) engaging latch (11).

FIG. 7 is a rear elevational view of the embodiment of an enclosing holder shown in FIG. 4. Dimensions of the exemplary embodiment are shown in inches. Torsion springs (9) are positioned at the hinge formed with holder top and base hinge portions (8 and 10, respectively).

FIG. 8 is a top plan view of the embodiment of an enclosing holder shown in FIG. 4. Dimensions of the exemplary embodiment are shown in inches. In the embodiment shown, enclosing holder top (6) comprises Schrader valve (14), integrated hinge portions (8) and an integrated handle (7) comprising slip resistance features (e.g., ridges) (7a).

FIG. 9 is a bottom plan view of the embodiment of an enclosing holder shown in FIG. 4. In the embodiment shown, holder base (5) comprises a plurality of feet (20).

FIG. 10 is a top perspective view of the embodiment of an enclosing holder shown in FIG. 4. In the embodiment shown, enclosing holder top (6) comprises integrated hinge portions (8) and an integrated handle (7) comprising slip resistance features (7a). Holder base (5) comprises integrated hinge portions (10) mated to the hinge portions (8) of top (6). In the embodiment shown, holder base (5) comprises external impressions (19).

FIG. 11 is a bottom perspective of the embodiment of an enclosing holder shown in FIG. 4. In the embodiment shown, the eight evenly-spaced feet (20) comprise threaded holes (21) for secure mounting of the holder to a surface in or on a mechanical shaker, e.g., a hub or platform in a mechanical shaker.

DEFINITIONS

Figure 1:
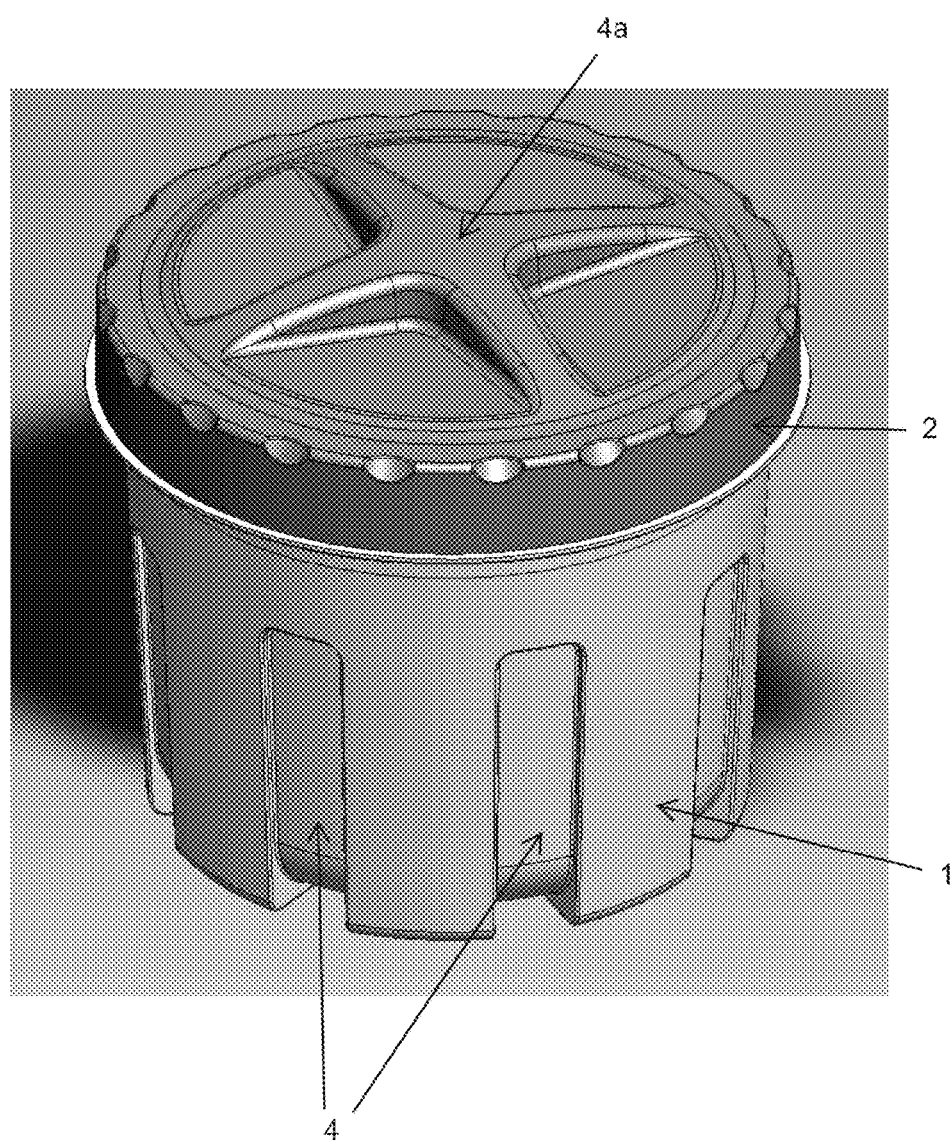
FIG. 1 is a drawing of an embodiment of an ergonomic sample container comprising a bucket (1) having gripping features (4), and a lid (2) having a central crossed gripping feature (4*a*).

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, the term "analyte" is to be construed broadly as any compound, molecule, element, ion, or other substance of interest to be detected, identified, or characterized.

As used herein, the terms "subject" and "patient" refer to an animal, preferably a human, from which a stool specimen is collected. In some instances, the subject is also a "user" (and thus the user is also the subject or patient).

As used herein, the transitional phrase "consisting essentially of" as used in reference to compositions, steps, or other features is to be read as "consisting of" the specified materials, steps, or features, plus only unavoidable additional elements that do not materially affect the basic and novel characteristic(s) of the materials, methods, steps, etc., e.g., unavoidable contaminants, unavoidable steps.

As used herein, the term "sample" and "specimen" are used interchangeably, and in the broadest senses. In one sense, sample is meant to include a specimen or culture obtained from any source, as well as biological and environmental samples. Biological samples may be obtained from animals (including humans) and encompass fluids, solids, tissues, and gases. Biological samples include blood products, such as plasma, serum, stool, urine, and the like.

Environmental samples include environmental material such as surface matter, soil, mud, sludge, biofilms, water, crystals, and industrial samples. Such examples are not however to be construed as limiting the sample types applicable to the present invention.

As used herein, the term "kit" refers to any delivery system for delivering materials. In the context of sample collection systems, such delivery systems include systems that allow for the storage, transport, or delivery of devices or the samples collected therewith (e.g., buffers, stabilizers, preservatives, etc. in the appropriate containers) and/or supporting materials (e.g., written instructions for performing a procedure, etc.) from one location to another. For example, kits include one or more enclosures (e.g., boxes) containing the relevant devices and supporting materials. As used herein, the term "fragmented kit" refers to a delivery system comprising two or more separate containers that each contains a subportion of the total kit components. The containers may be delivered to the intended recipient together or separately. For example, a first container may contain materials for sample collection and a buffer, while a second container contains sampling devices, separate shipping materials, etc.

The term "system" as used herein refers to a collection of articles for use for a particular purpose. In some embodiments, the articles comprise instructions for use, as information supplied on e.g., an article, on paper, or on recordable media (e.g., diskette, CD, flash drive, etc.). In some embodiments, instructions direct a user to an online location, e.g., a website, a remote server of a service provider, etc.

The term "ergonomic" as used herein in reference to designs or features, e.g., of an article or system, refers to designs or features optimized for use by the intended human user, e.g., to avoid unnecessary stress, fatigue, or unintended improper use, or to accommodate special needs of a human user. For example, a device having ergonomic features optimized for geriatric users may have features especially designed or selected to accommodate conditions and/or disabilities common in a population of geriatric persons, e.g., arthritis, muscle weakness, carpal tunnel syndrome, epicondylitis, vision impairment, etc.

As used herein, the term "central axis," as used in reference to a container or ergonomic device, refers to an axis about which the container device has rotational symmetry. For example, in ergonomic devices depicted in FIGS. 1-3, the central axis is defined by the line between the point at the center of the bottom of the bucket and the point at the center of the lid, when the lid is engaged with the bucket.

The term "geriatric" as used in reference to a subject or patient or a user of a device, refers to an aged or elderly person, e.g., a person over about 65 years of age. There is no defined age for "geriatric" thus in some instances it may be e.g. a person over about 50 years of age.

DETAILED DESCRIPTION OF THE INVENTION

Embodiments of the invention are described in this Detailed Description of the Invention, and in the Summary above, which is incorporated here by reference. Although the invention has been described in connection with specific embodiments, it should be understood that the invention as claimed should not be unduly limited to such specific embodiments. Those skilled in the art who review this disclosure will readily appreciate that many modifications are possible (e.g., variations in sizes, dimensions, structures, shapes and proportions of the various elements, values of parameters, mounting arrangements, use of materials, orientations, etc.) without materially departing from the novel teachings and advantages of the subject matter of the technology. Accordingly, all such modifications are intended to be included within the scope of the present invention as defined in the appended claims.

Provided herein is technology relating to processing samples and particularly, but not exclusively, to technology for processing a collected stool specimen. In particular, the technology is directed to processing specimens in sample containers received from subjects or patients who have collected stool samples, e.g., their own or a family member's, in the home.

A particular challenge when subjects or patients collect stool samples is the need for a collection container that is 1) sufficiently easy to manipulate that the container can be reliably and securely closed and sealed by subjects who may have conditions and/or disabilities that make manipulating containers difficult, e.g., arthritis, muscle weakness, carpal tunnel syndrome, epicondylitis, vision impairment, etc., but that, 2) when closed, is sealed with a sufficiently reliable seal that there is little or no chance of leakage during transport and/or downstream processing, e.g., shaking homogenization. As discussed above, such collections may be facilitated by the use of an ergonomic container, e.g., as provided in International Patent Publication WO 2015/031832, which is incorporated herein by reference in its entirety for all purposes.

Provided herein is technology directed to improved safety and efficiency in processing collected specimens, e.g., in a clinical or research lab. The technology thus provides systems and methods for processing a stool sample, e.g., by dispersing or homogenizing the stool in buffer, directly in the sample container in which it has been collected by a subject, without the need to transfer the sample to a different container, or even to open the collection container received from the subject. The technology provides an enclosing holder to support and contain a sealed sample collection container, e.g., during mechanical shaking. In preferred embodiments, the technology is directed to processing samples in ergonomic sample containers such as the exemplary embodiments portrayed in FIGS. 1-3, in which the bucket of the container comprises gripping features designed to facilitate grasping of the bucket by an adult person with limited hand size and/or strength, e.g., a geriatric patient, such that the container can be closed and sealed by hand by such an person. In particularly preferred embodiments, the gripping features on the bucket are of sufficient depth and placement around the circumference of the bucket that the bucket may be approached from essentially any direction, and the bucket may be securely gripped by holding gripping features that span less than one half the circumference of the bucket, preferably less than one third the circumference of the bucket.

The containers further include features configured to facilitate mixing the contents within the sealed container without opening the container, e.g., through agitation of the sealed container (by, e.g., shaking, rotating, vibrating, etc.). For example, the sample container may comprise interior ridges, bumps, or other features that intrude into the interior space within the closed container. Containers are typically constructed of unbreakable material, e.g., plastic and/or rubber. Suitable materials may be natural or synthetic, and include but are not limited to, e.g., polypropylene, polyethylene, polycarbonate, polystyrene, polyvinylchloride, polyamides, etc. In certain embodiments, the bucket has an internal volume of at least 300 ml, and in preferred embodiments, said bucket has an internal volume between about 300 ml and about 1400 ml. In certain embodiments, the bucket has an opening that is at least as wide as the height of the bucket. In some embodiments, the diameter of the opening (e.g., the internal diameter, ID), is greater than or equal to the height of the bucket.

The technology provides an enclosing holder adapted to receive and enclose a sample container during processing manipulations conducted for mixing contents within the sealed container, e.g., agitation of the sealed container (by, for example, shaking, rotating, vibrating, gyroscopic mixing, etc.). In some embodiments, the enclosing holder is configured to securely seal, such that any contents leaking from a sample container, e.g., during vigorous agitation, are completely contained within the enclosing holder, thereby reducing risk of accidental worker exposure to leaked biological samples.

Figure 2:
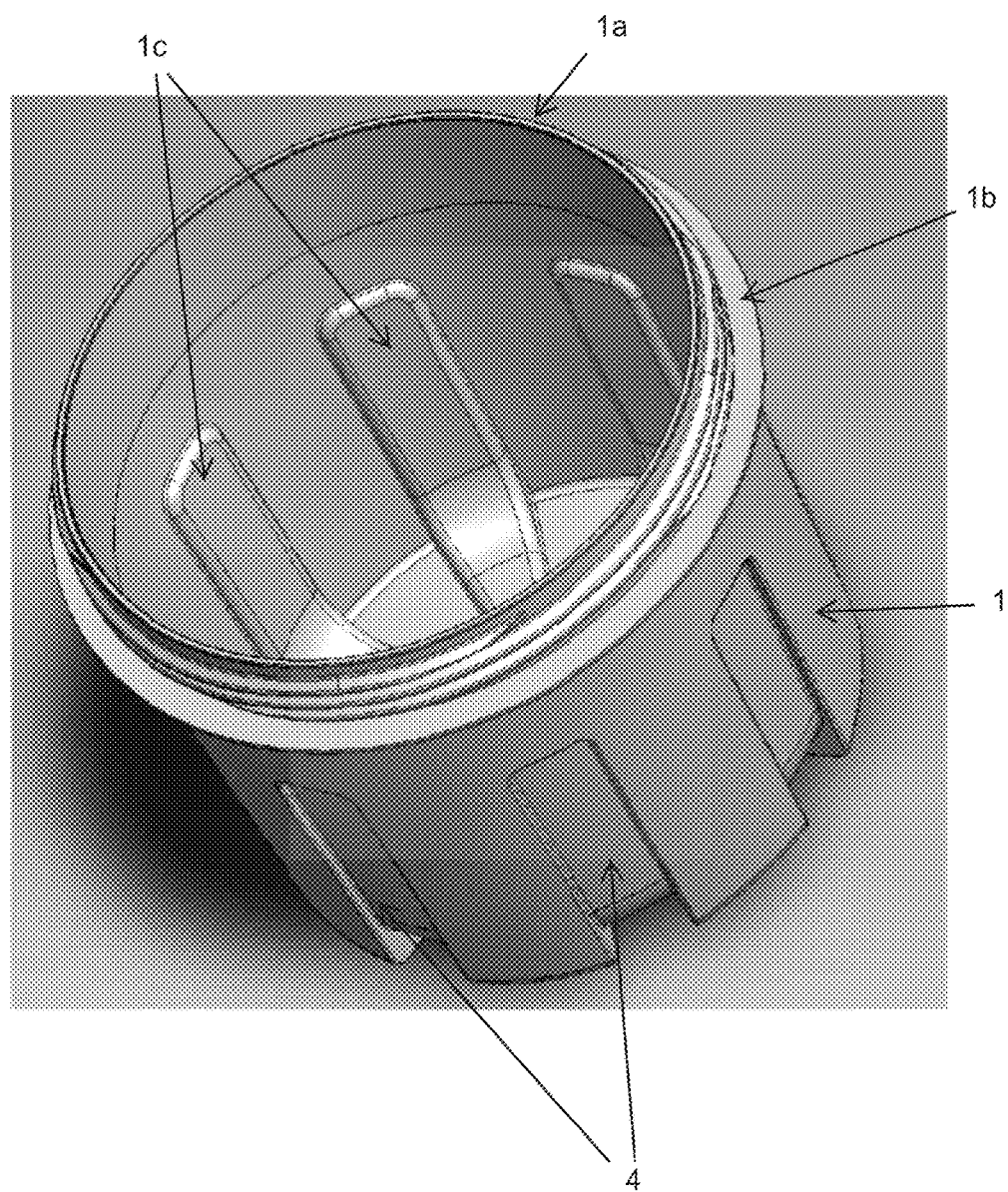
FIG. 2 is a perspective interior view of an embodiment of a bucket (1) showing a top surface (1*a*), gripping features (4) and an engagement portion that is threaded. The interior of the bucket shows radially disposed ridges providing sample disruption features (1*c*).
Figure 12A:
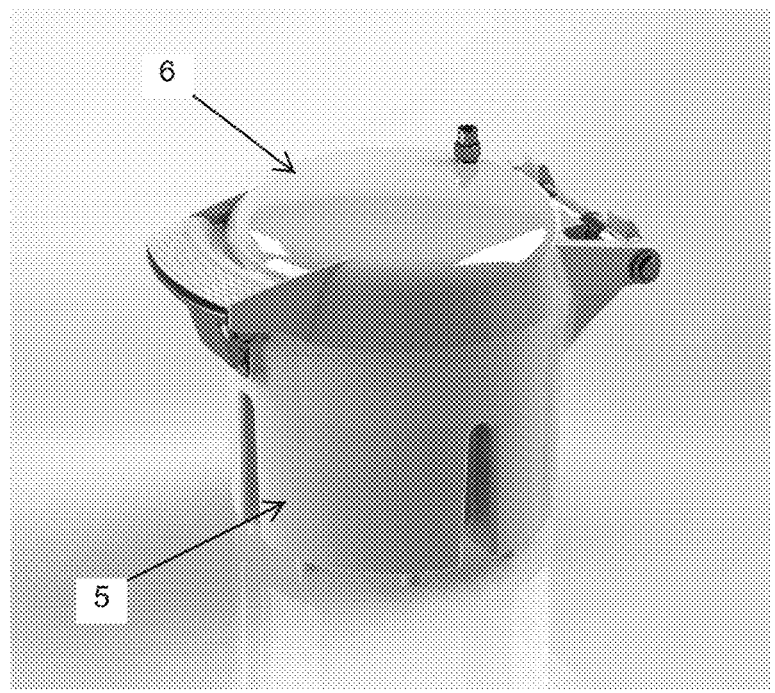
FIG. 12A shows a top perspective view of an embodiment of an enclosing holder.
Figure 12B:
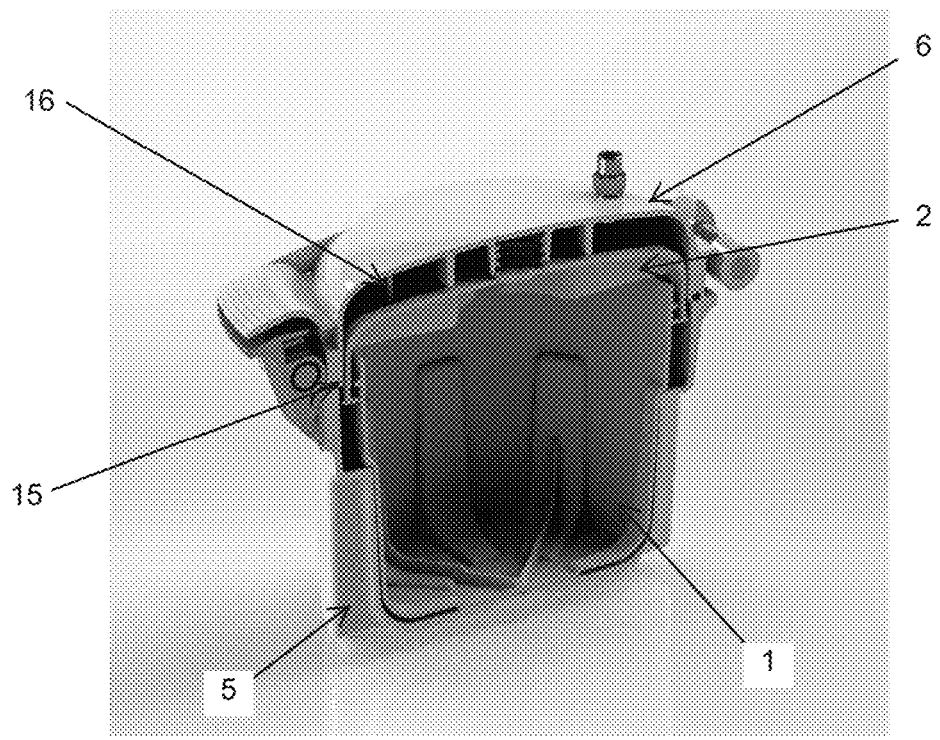
FIG. 12B shows a cross-sectional perspective view of an embodiment of an enclosing holder. In this view, a sample container comprising bucket (1) and top (2), also shown in cross section, is shown within the enclosing holder.
Figure 13A:
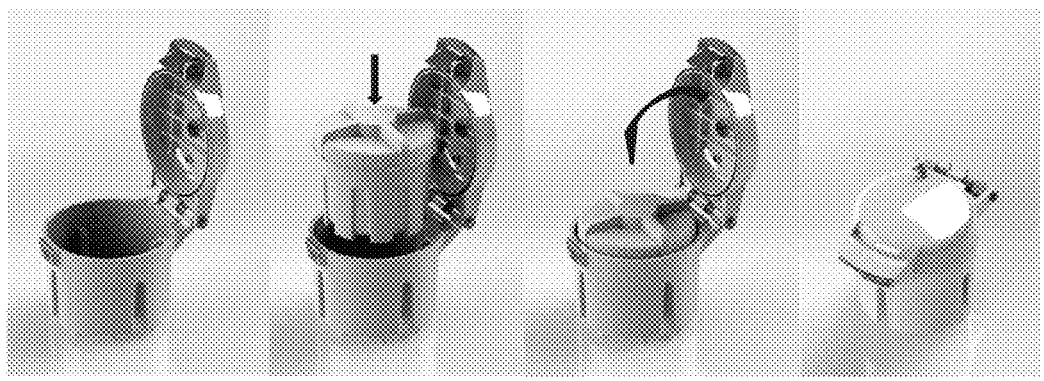
FIG. 13A shows steps of placing a sample container within an enclosing holder and closing the top.
Figure 13B:
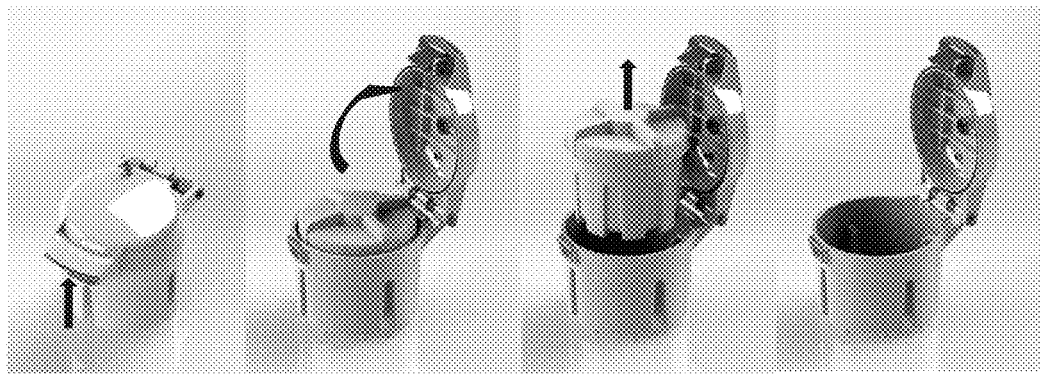
FIG. 13B shows steps of opening an enclosing holder and removing a sample container therein from the enclosing holder.
Figure 14:
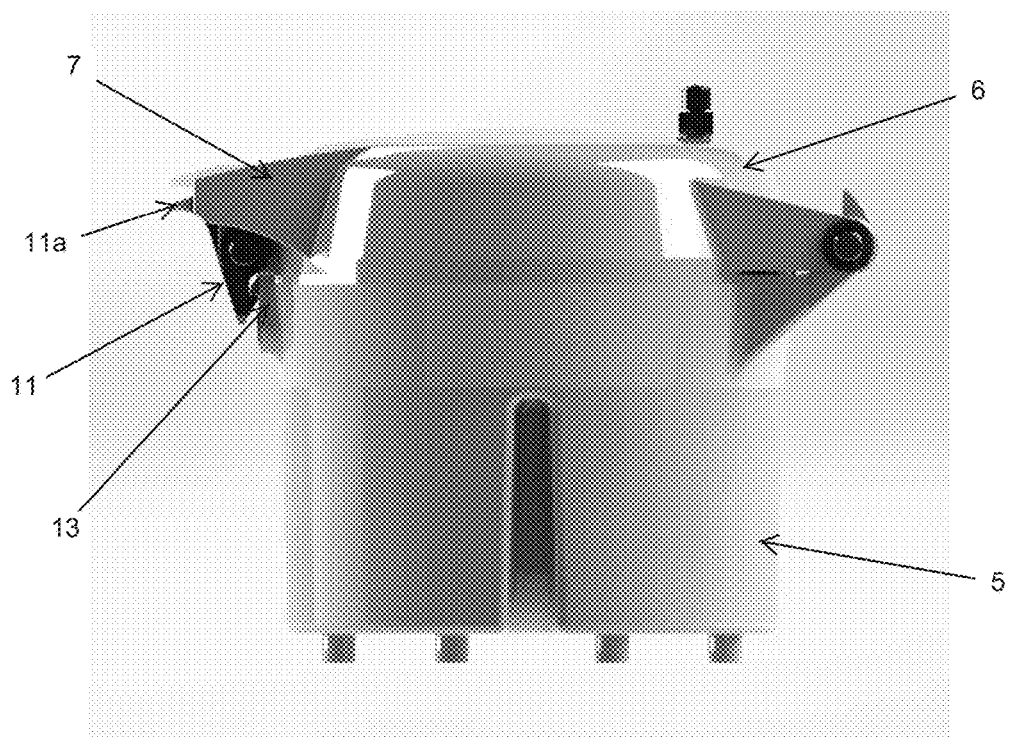
FIG. 14 shows an embodiment of an enclosing holder in a closed state. In the embodiment shown, top (6) of the enclosing holder comprises an integral handle (7) and a latch (11). As depicted, latch (11) comprises a latch release (11a) that can be actuated, e.g., lifted, to disengage latch (11) from catch (13) on holder base (5). In some embodiments the top (6) comprises a spring, e.g., a compression or torsion spring (9) in the handle (7), to maintain latch (11) in a position to engage catch (13), e.g., when the latch is in an engagement position and when there is an absence of pressure (e.g., by a user) on latch release (11a). In preferred embodiments, latch release (11a) is an integral portion of latch (11).
Figure 16:
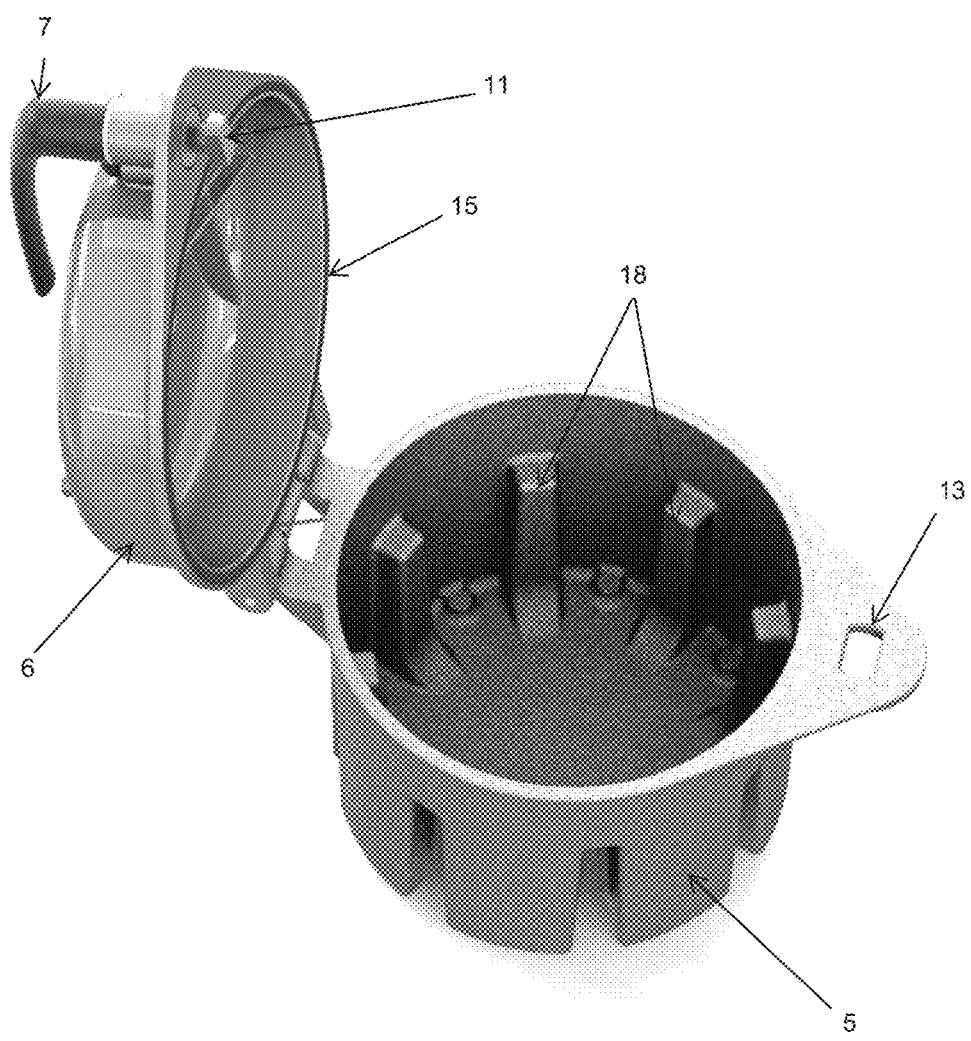
FIG. 16 shows a top perspective view of an embodiment of an enclosing holder in an open configuration. Within the interior of holder base (5), integrated container-engaging features (18) (e.g., for engaging the gripping features (4) of a sample container as shown in FIG. 1) are shown. In the embodiment shown, the latch (11) comprises a latch pin configured to mate and engage with a keyhole-style latch pin hole as a catch (13).

In preferred embodiments, an enclosing holder is configured with internal features that mate to external features on the sample container, such that a sample container is securely held within the enclosing holder when the enclosing holder is secured in a closed state. For example, FIG. 16 shows in interior view of an embodiment of an enclosing holder, the base (6) of the holder having integrated container-engaging features (18). FIG. 12B shows a cross-sectional view of an embodiment of an enclosing holder that comprises ridges configured to mate with gripping features (4) on the exterior of a sample container as shown in FIGS. 1-3.

When a sealed container is fitted within a closed enclosing holder, rotational movement of the bucket within the enclosing holder e.g., around a central axis, is restricted or, preferably, prevented. The number of container-engaging features present in the enclosing holder need not match the number of external features (e.g., gripping features (4)) on the sample container. It is contemplated that one or any subset of the external features on the exterior of a sample container may be mated with a container-engaging feature within the top and/or base of an enclosing holder.

In some embodiments, an enclosing holder comprises a holder top (6) attached to holder base (5), e.g., via a hinge. In preferred embodiments, the holder top (6) and/or the holder base (5) comprise integrated hinge portions ((8) and (10), respectively) that together form a hinge attaching the top to the base. As used herein, the terms "integrated" and "integral," as used in reference to hinges, handles, and other features of a holder top and/or holder base, are used interchangeably to refer to features that are attached to the top or base in a non-movable, non-removable manner, e.g., that are cast as part of the top or base, or are machined into the top or base. In some embodiments, integrated features may be separately manufactured and then affixed to an existing top or base, e.g., by brazing or welding. In preferred embodiments, the holder base and/or the holder top are cast with integrated components, e.g., hinge portions, in place.

Technology herein provides an enclosing holder configured for particular ease of use, and configured to avoid accidental misuse, e.g., in a laboratory environment. In preferred embodiments, the technology provides an enclosing holder comprises a feature, e.g., a spring, which holds the holder top (6) in a clearly open position when the holder top (6) is not engaged to the holder base (5), e.g., when a latch (11) on the holder top (6) in not engaged with a corresponding catch (13) on the holder base (6). As used herein, a "clearly open position" may be partially open or fully open, e.g., to the limit permitted by the hinge, so long as simple inspection, e.g., momentary visual inspection, shows that the holder is not closed and the holder top is not engaged to the holder base. Thus, the technology provides an enclosing holder configured to reduce or eliminate the possibility of an enclosing holder containing a sample container being shaken (e.g., in a mechanical shaker) when the holder top (6) is not properly seated and latched to the holder base (5).

Figure 6:
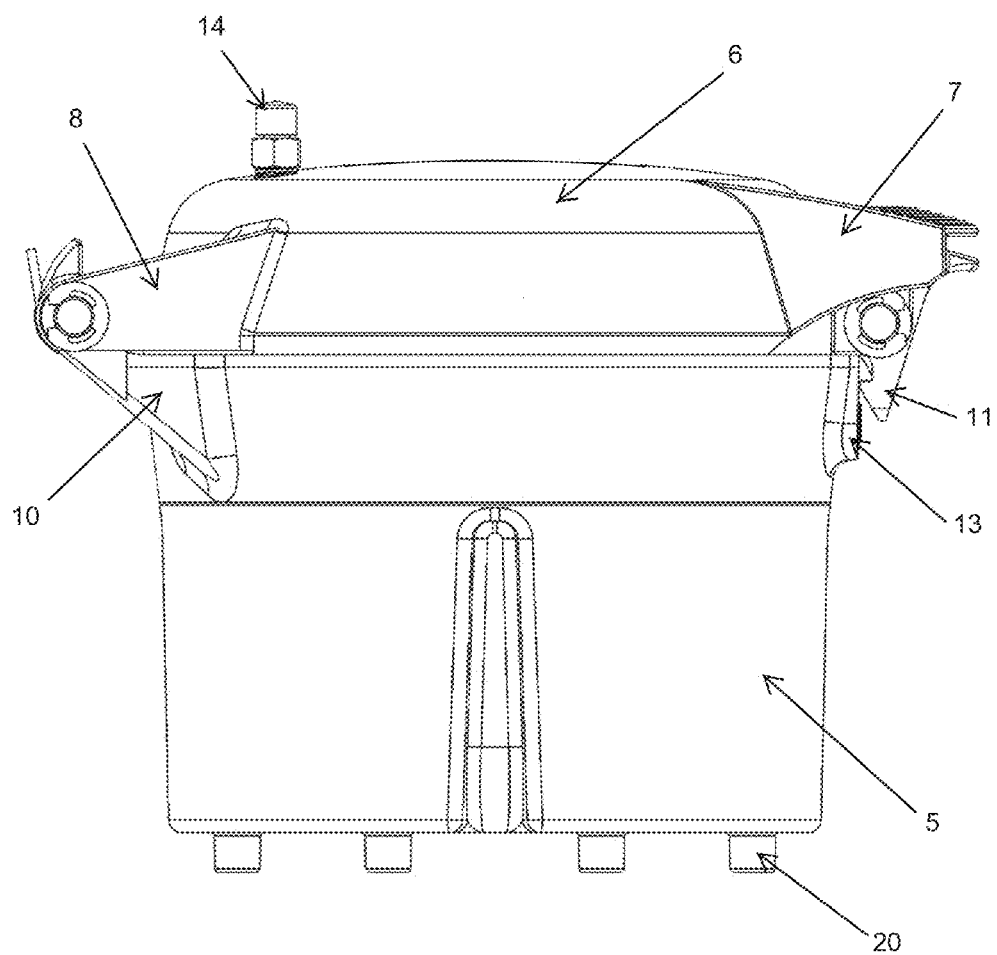
Figure 7:
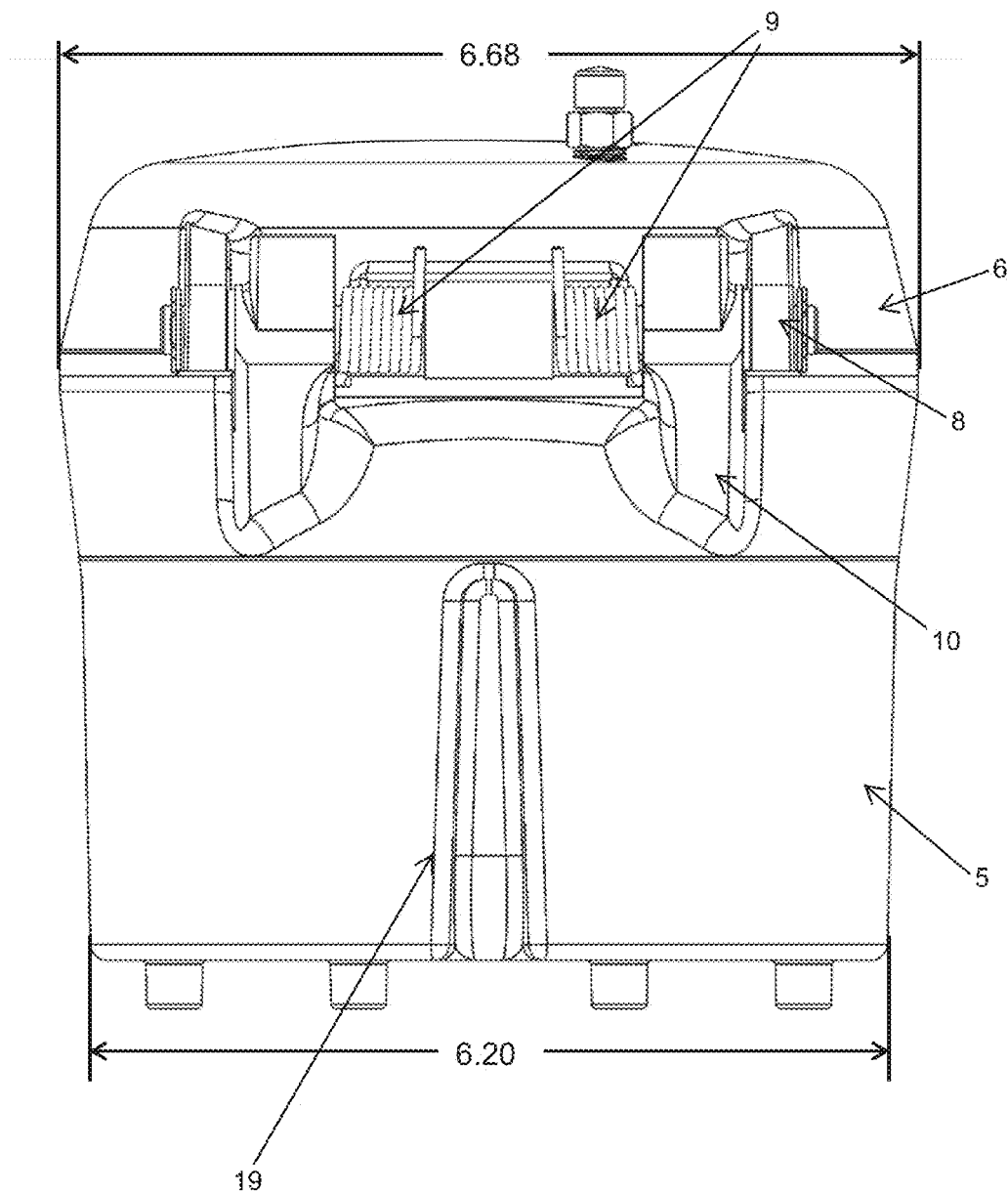
Figure 8:
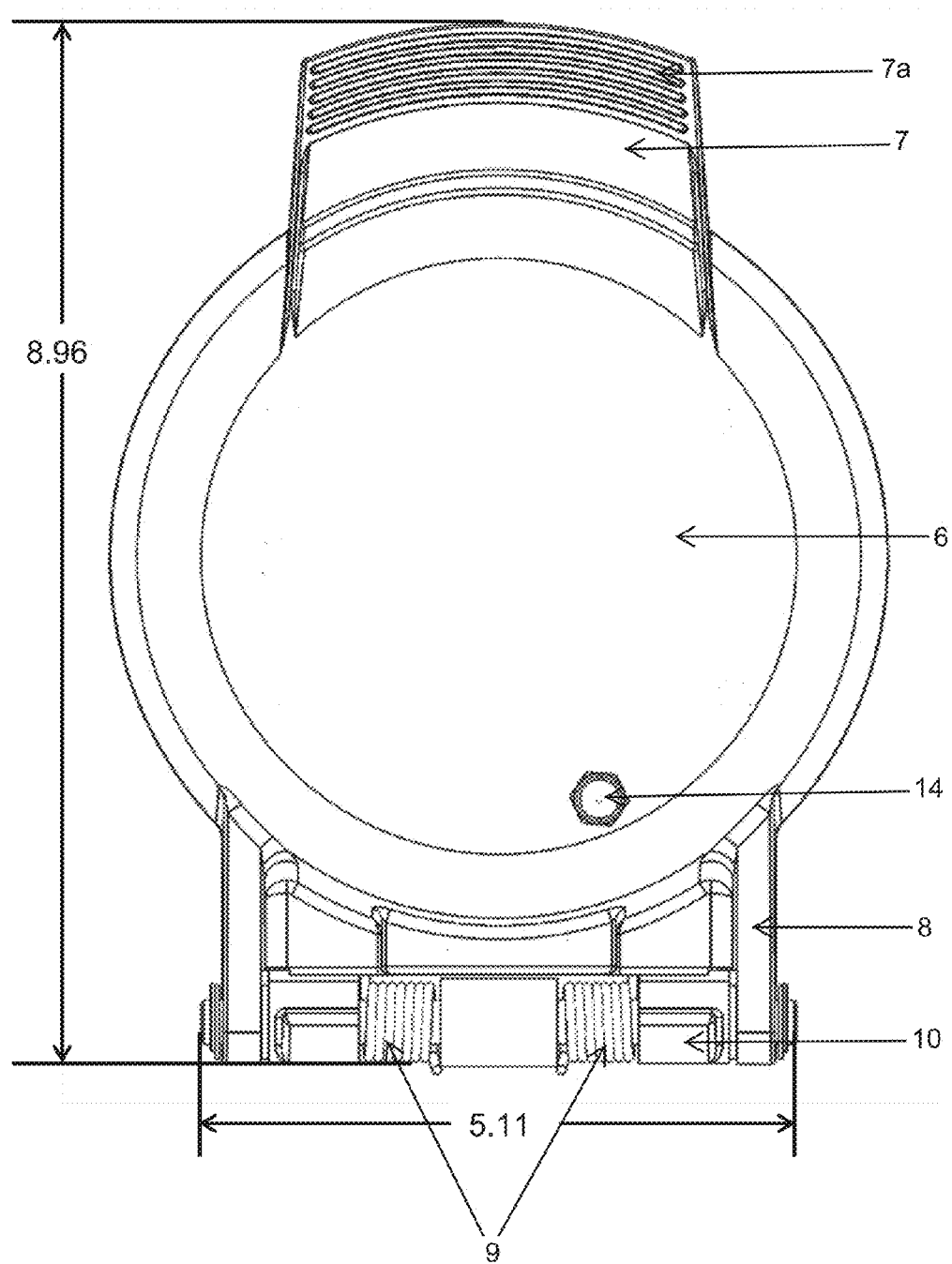

As used herein, the terms "latch" and "catch" refer to mated latching engagement features on a top (6) and base (5), respectively, of an enclosing holder, and are not limited to particular structural features. For example, a hook-shaped feature, e.g., as shown on latch (11) on top (6) in FIG. 6, if used on a base (5) would be termed a "catch".

In some embodiments, a holder top (6) comprises a handle (7) and a latch (11) for latching engagement of the top (6) to the base (5) of the enclosing holder when the enclosing holder is in a closed configuration. For example, in some embodiments, when the holder top is positioned on the top of the holder base in preparation for sealing, and the top is then pressed upon the base, a latch (11) on the holder top engages a catch (13) on the holder base to engage the enclosing holder in a closed configuration. In preferred embodiments, pressing on the holder top to seat the top on the base is sufficient to engage the latch to the catch, and to seal the enclosing holder.

Figure 9:
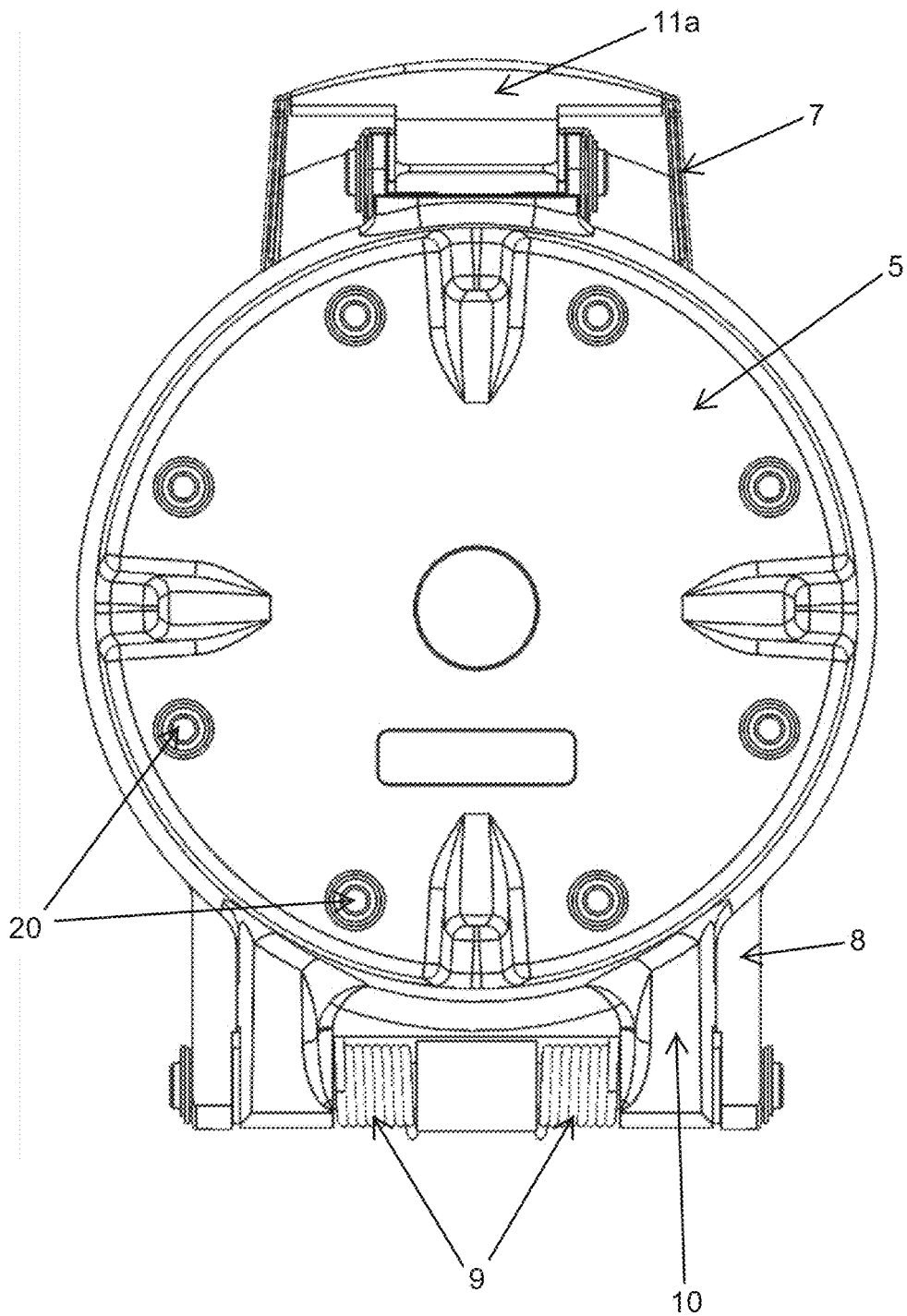
Figure 10:
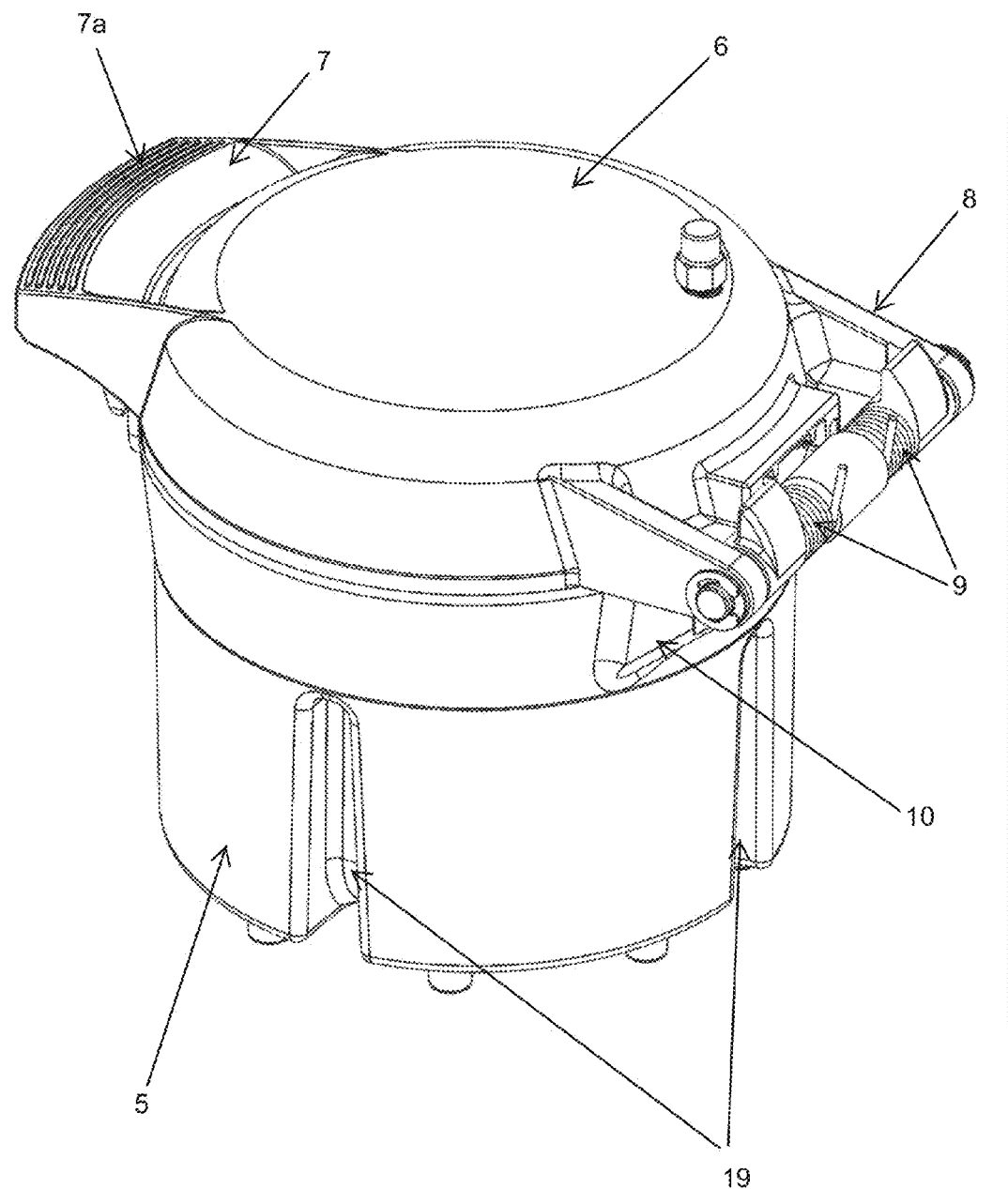
Figure 11:
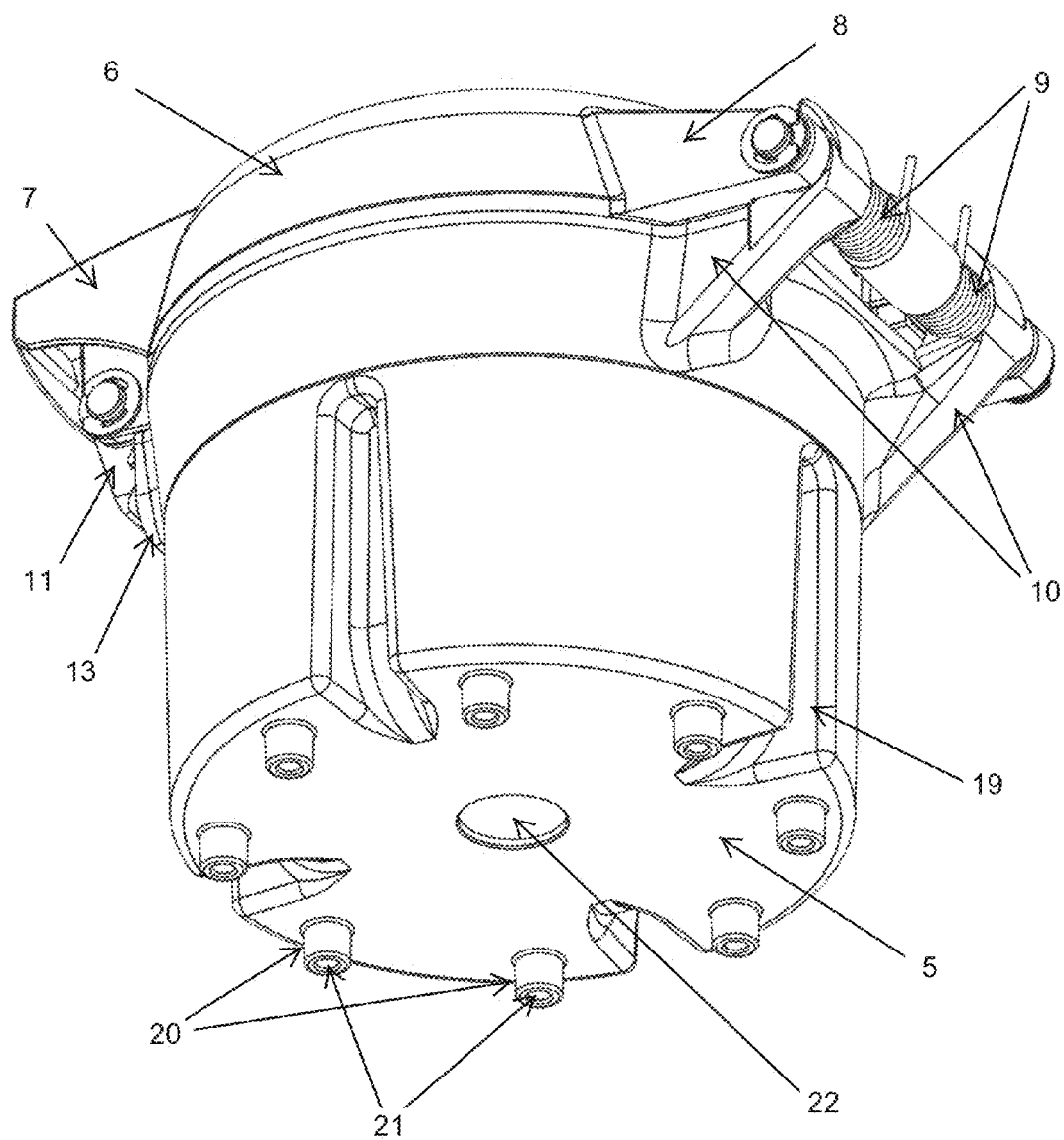

In some embodiments, the mated latching engagement features on the top and base of the enclosing holder comprise a latch release. In preferred embodiments, the enclosing holder comprise a latch release (11a) configured, e.g., with a spring, to maintain the latch release in an unreleased position until the latch release is actuated or pressed by a user. A latch release (11a) is not limited to any particular configuration or size. In certain preferred embodiments, the latch release covers a substantial portion the underside of a handle (7), e.g., so that it is readily actuatable by applying upward pressure from below the handle. For example, as shown in FIG. 9, the latch release (11a) spans substantially the full width of the underside of handle (7). In particularly preferred embodiments, latch release (11a) is actuatable with one hand, e.g., without the need to secure or restrain the enclosing holder with a second hand.

The technology provides an enclosing holder comprising container-engaging features. For example, in some embodiments, a lid-engaging feature (16) is configured to engage with lid (2) of a sealed container within the enclosing holder. In some embodiments, for example, the interior of the holder top (6) comprises lid engaging features (16) that engage crossed gripping features (4a) on lid (2), as exemplified in the container shown in FIG. 1. In preferred embodiments, the lid engaging features (16) and bucket-engaging features (18) in the interior of the holder base are configured to restrict or prevent any movement, e.g., rotation, of lid (2) relative to bucket (1) of a sealed sample container when the sealed sample container is secured inside a closed enclosing holder.

In some embodiments, an enclosing holder is configured to apply pressure to the bottom and/or the top of the sealed container, e.g., to limit any motion of the sealed container within the enclosing holder, and/or to support or reinforce the seal between the bucket (1) and lid (2) of the sample container that is within the enclosing holder. For example, in some embodiments, one or more compression springs (17) are included in the bottom of the enclosing holder base and/or the holder top to maintain a compressive pressure upon the sealed container that is within a closed enclosing holder. In preferred embodiments, the enclosing holder provides pressure on the sample container that is in alignment with the central axis of the sealed container, so as to press lid (2) toward bucket (1), and vice versa. In particularly preferred embodiments, the enclosing holder has a compression spring (17) in the top (6) of the enclosing holder, while in some embodiments, the pressure is applied via, e.g., a resilient material such as rubber or plastic, open or closed cell foam, padding, etc.

In some embodiments, e.g., as shown in FIGS. 15-19, engagement of mated latching engagement features on the holder's top and base is accomplished by rotation of a handle attached to a latch. For example, in some embodiments, the holder top (6) and holder base (5) comprise mated latching engagement features, e.g., as shown in FIG. 16, which are engaged by twisting the handle from a first position into a second position so as to permit latch (11) to pass through an opening in catch (13), then moving the handle to a position, e.g., back to the first position, in which the latch (11) is engaged to the catch (13). In preferred embodiments, when holder top (6) is seated on the holder base (5), returning handle (7) to the first position engages latch (11) to the catch (13). In particularly preferred embodiments, the handle arrangement is equipped, e.g., with a spring, to maintain the handle in the first (latched) position when a user is not actuating the engagement or latch release functions.

Figure 15:
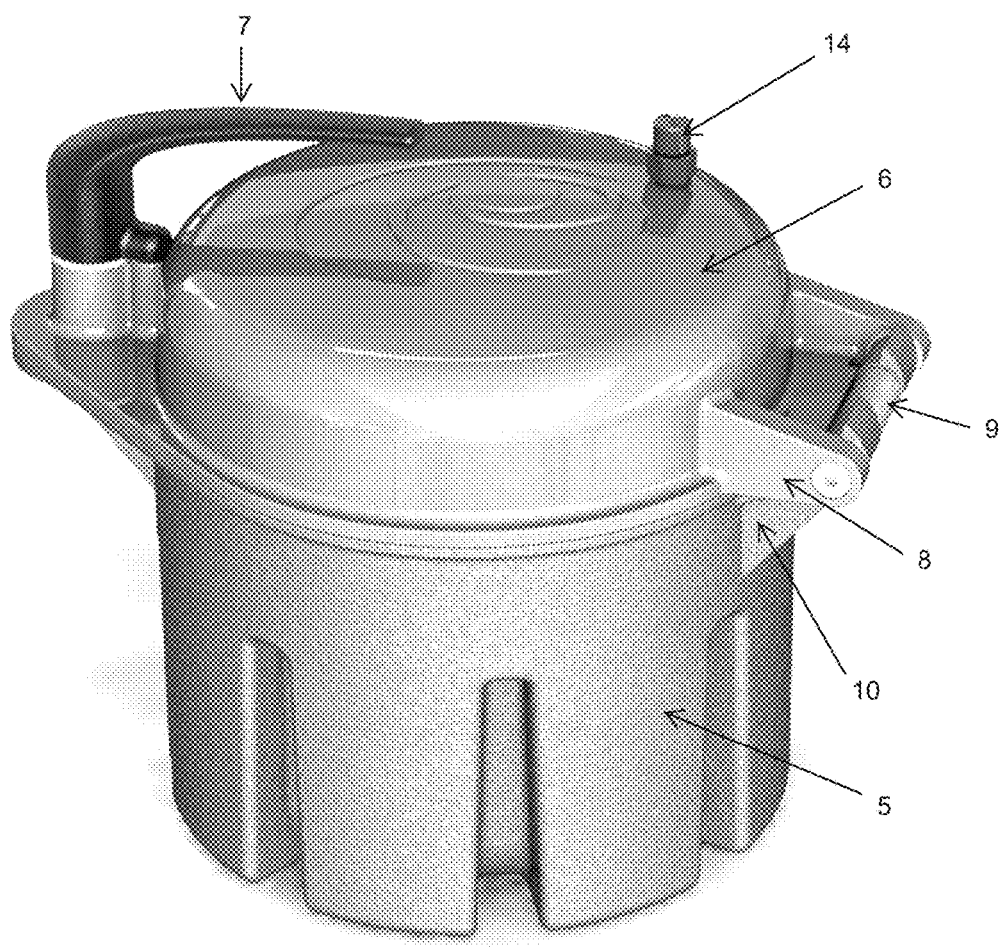
FIG. 15 shows a top perspective view of an embodiment of an enclosing holder in a closed configuration.
Figure 17:
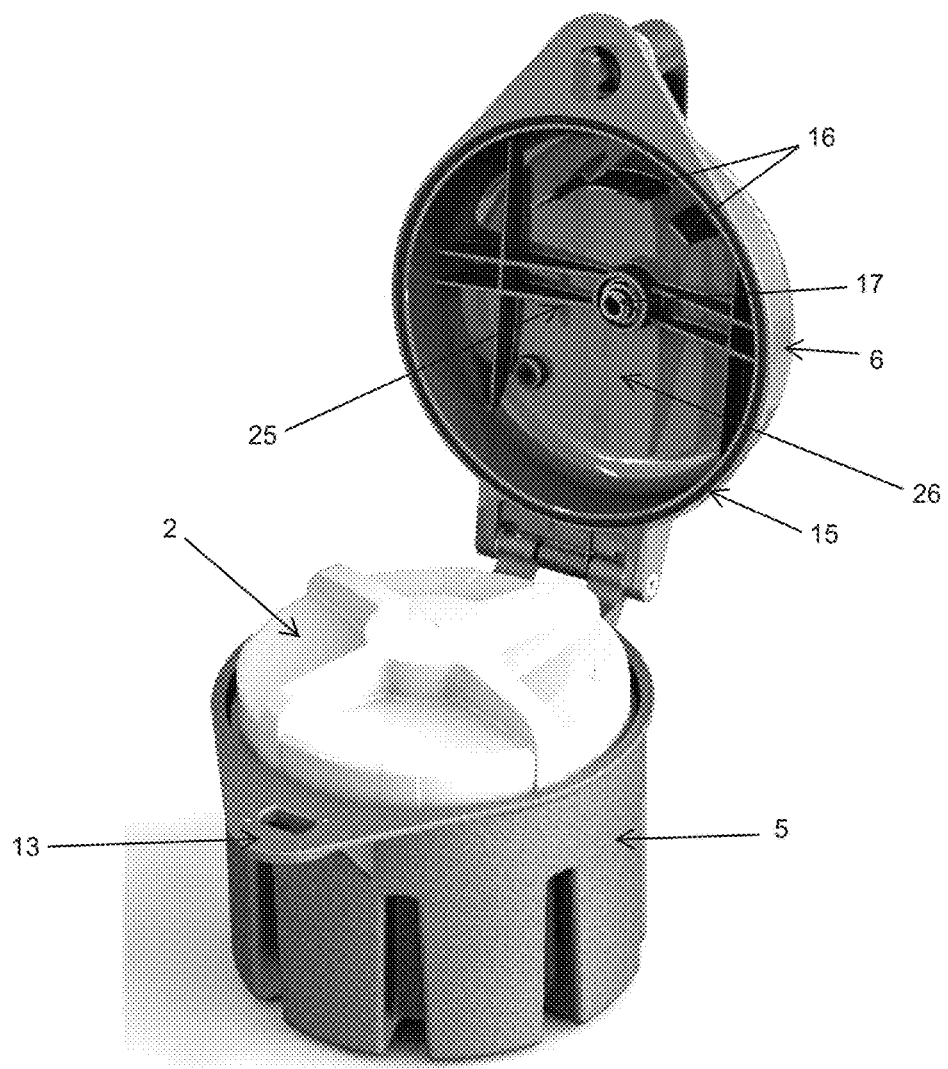
FIG. 17 shows an embodiment of an enclosing holder with a container in place in the base of the holder. In the embodiment shown, holder top (6) comprises an O-ring (15) that provides a seal between the holder top (6) and base (5) when the enclosing holder is in a closed position. The holder top (6) further comprises a compression spring (17) that exerts downward pressure on the center of lid (2) of a sample container and lid engaging features (16) that prevent rotation of lid (2) with respect to bucket (1) of the sample container, when the sealed sample container is enclosed within the enclosing holder. Integral ribs (25) in the holder top further secure the sample container.
Figure 18:
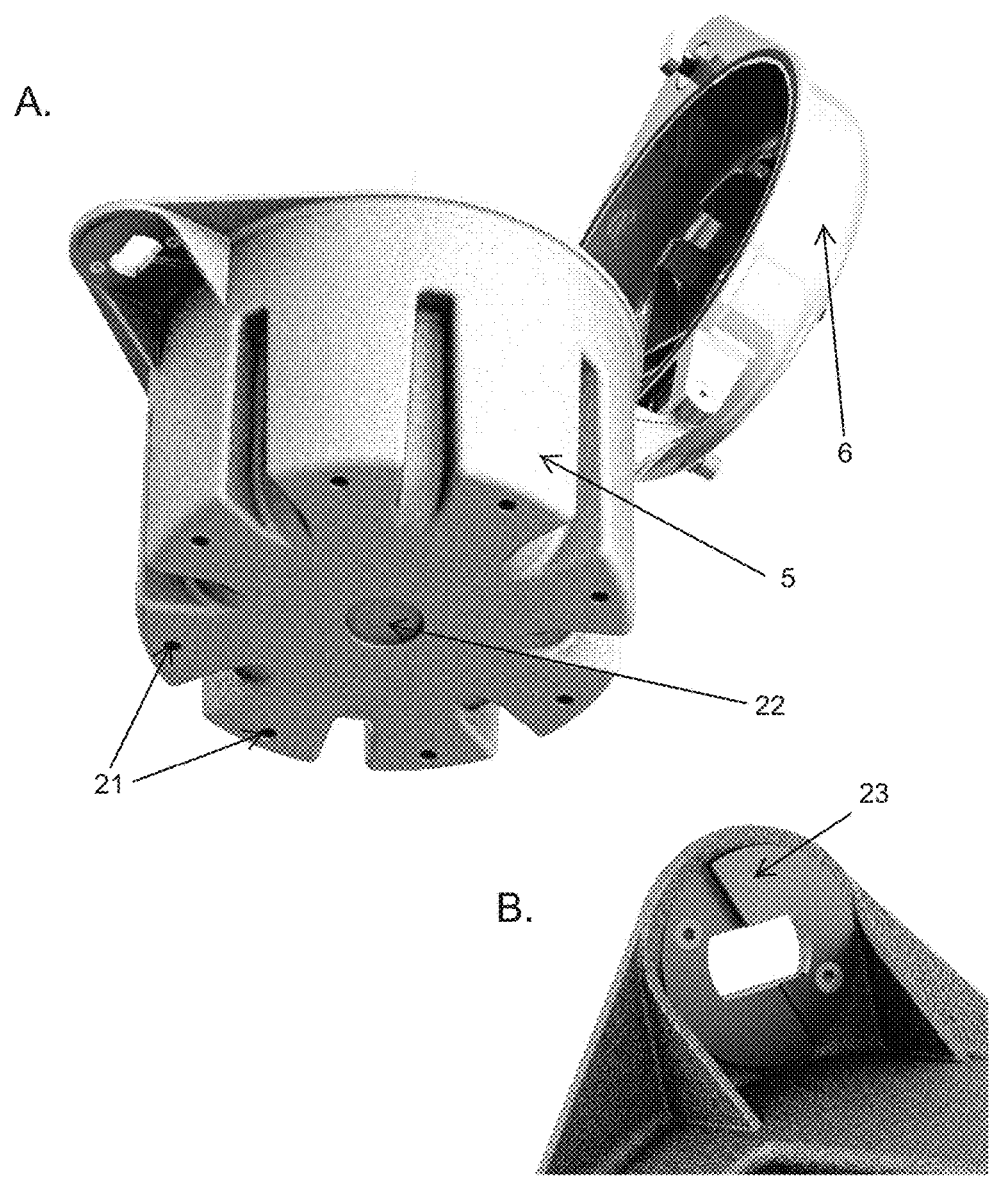
FIG. 18A shows a bottom perspective view of an embodiment of an enclosing holder. In the embodiment shown, eight evenly-spaced threaded holes (21) are provided for secure mounting of the holder to a surface, e.g., a hub or platform in a mechanical shaker. A machined pilot counterbore hole (pilot hole (22)) is provided to facilitate proper alignment of the enclosing holder during mounting of the holder in the shaker.
FIG. 18B provides a detail view of the underside of the latch pin hole of the embodiment shown in FIG. 18A, showing a cam plate (23) for secure engagement of the latch pin with the latch pin hole.
Figure 19:
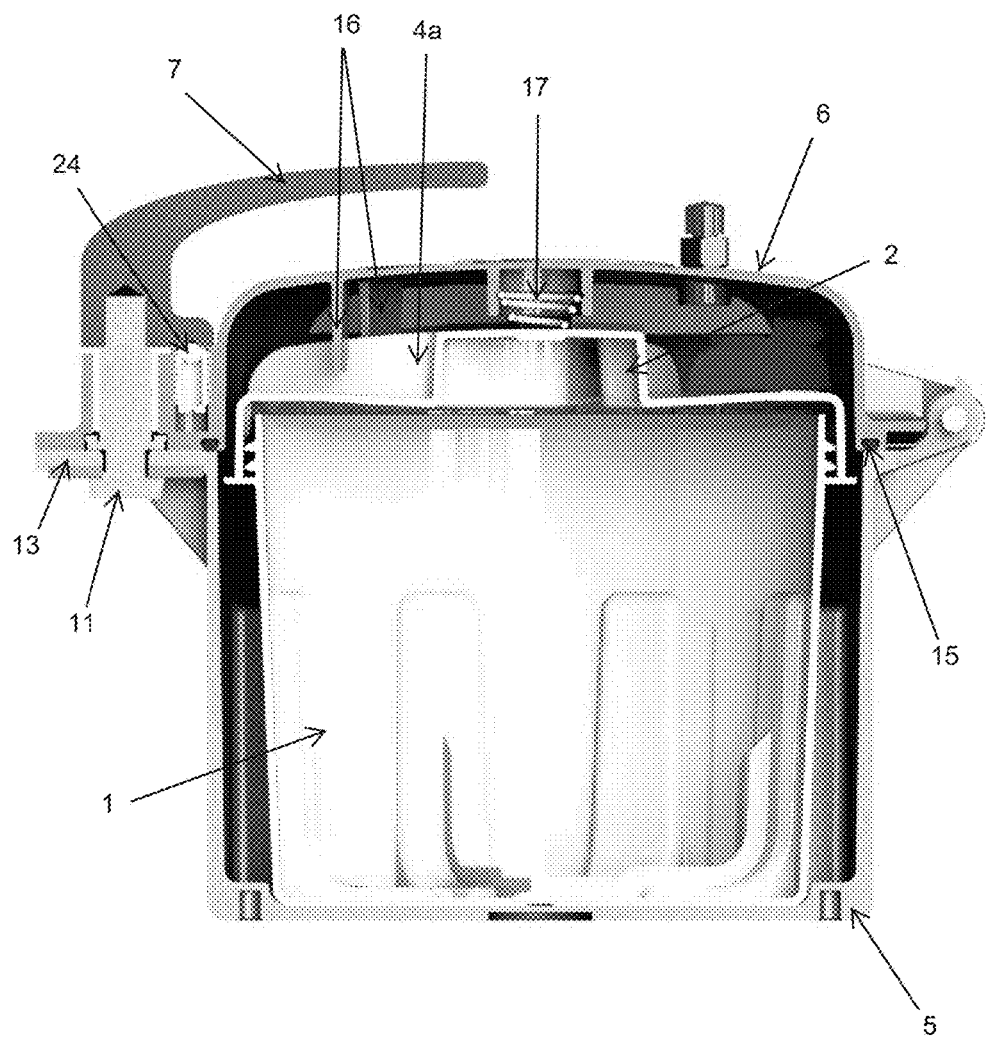
FIG. 19 shows a cross-sectional view of an embodiment of an enclosing holder. In this view, a sample container, also shown in cross section, is shown within the closed enclosing holder. Container-engaging features (16) in holder top (6) are shown engaged with gripping features (4a) on the lid (2) of the sample container. A ball-nose detent spring (24) and a countersink in the bottom of handle (7) allows ball to "click" into position, preventing handle movement.

In preferred embodiments, an enclosing holder comprises a gasket that is disposed between the holder top (6) and the holder base (5) when the enclosing holder is in a closed configuration. For example, in some embodiments, the holder base (5) and/or top (6) comprise an O-ring seal (15), e.g., as shown in FIGS. 12B, 15, and 17. In preferred embodiments, the holder top (6) comprises an O-ring seal fitted in a suitable groove at or near the perimeter of the holder top, e.g., as shown in FIG. 17. The O-ring seal is not limited to any particular material and may be, e.g., rubber, plastic, etc. In preferred embodiments, the O-ring seal is composed of silicone. In some embodiments, the O-ring seal is Shore 50A durometer for low compression force and is mounted in machined dovetail groove.

In some embodiments, an enclosing holder comprises a port or valve for altering the gas contents of a closed enclosing holder. For example, in some embodiments, it is useful to create a negative pressure within the holder as a means of preventing out-flow of contents in the event of a leak from an enclosed container, while in other embodiments it is useful to vent pressure, e.g., pressure arising from an increase in temperature within the sealed enclosing holder. In some embodiments, it may be useful to introduce a particular gas, e.g., an inert gas such as nitrogen, into the vessel. To facilitate the movement of gases into or out of a sealed enclosing holder without opening the vessel, in certain preferred embodiments, the enclosing holder comprises a suitable valve, e.g., a Schrader valve (14), for adding or removing gas (e.g., air, nitrogen) from the enclosing holder when the enclosing holder is in a closed, e.g., locked, configuration.

In some embodiments, the enclosing holder is provided with one or more gripping features, to facilitate handling and manipulating the holder or lid, e.g., to facilitate the processes of closing the holder. For example, in some embodiments, the enclosing holder comprises ridges or other slip-resistance features or textures on a handle to reduce possible slippage, e.g., when closing or opening the enclosing holder, and/or when moving the holder in or out of a shaker device. In some embodiments, an enclosing holder comprises exterior channels, e.g., channels on the holder base that may be used for securing the holder base, either by hand or by using a device that engages the channels. Such exterior features are not limited to channels and may comprise surface features of any configuration, e.g., dimples, bumps, knobs, ridges, holes, etc. In preferred embodiments, exterior channels on the holder base align with container-engaging features on the interior of the holder base.

The enclosing holder is preferably constructed of unbreakable material, selected to withstand vigorous shaking, rotation, or other agitation used, e.g., in homogenizing a sample in a sealed sample container. For example, in preferred embodiments, the holder base (5) comprises or is composed of metal, e.g., stainless steel, aluminum, titanium, while in other embodiments, the base comprises or is composed of plastic. In particularly preferred embodiments, holder base (5) and/or top (6) are composed of aluminum. In preferred embodiments, the holder base (5) and/or top (6) are cast metal. In some embodiments, cast components are further processed, e.g., machined, to achieve a desired final form. In some embodiments, the holder top and/or older base are further surface-treated, e.g., coated, painted, enameled, or anodized.

The technology finds use in systems for processing a sample, e.g., a system comprising an enclosing holder in combination with, e.g., a mechanical shaker and/or a sample container.

Example 1

A. Sample Container

As discussed above, technology herein is directed to overcoming the challenge of providing a collection container that can be reliably used and sealed by any subject in a diverse population of subjects, including subjects having conditions that may severely compromise their ability to align and/or to firmly close a container, e.g., geriatric patients. For containers that are to be transported, e.g., from a subject's home to a laboratory, using standard commercial shipping methods, it is especially important for the subject to achieve a leak-resistant seal on the container without the need for special tools or assistance. As discussed above, technology herein provides an ergonomic collection device that can be securely closed using minimum force.

Figure 3D:
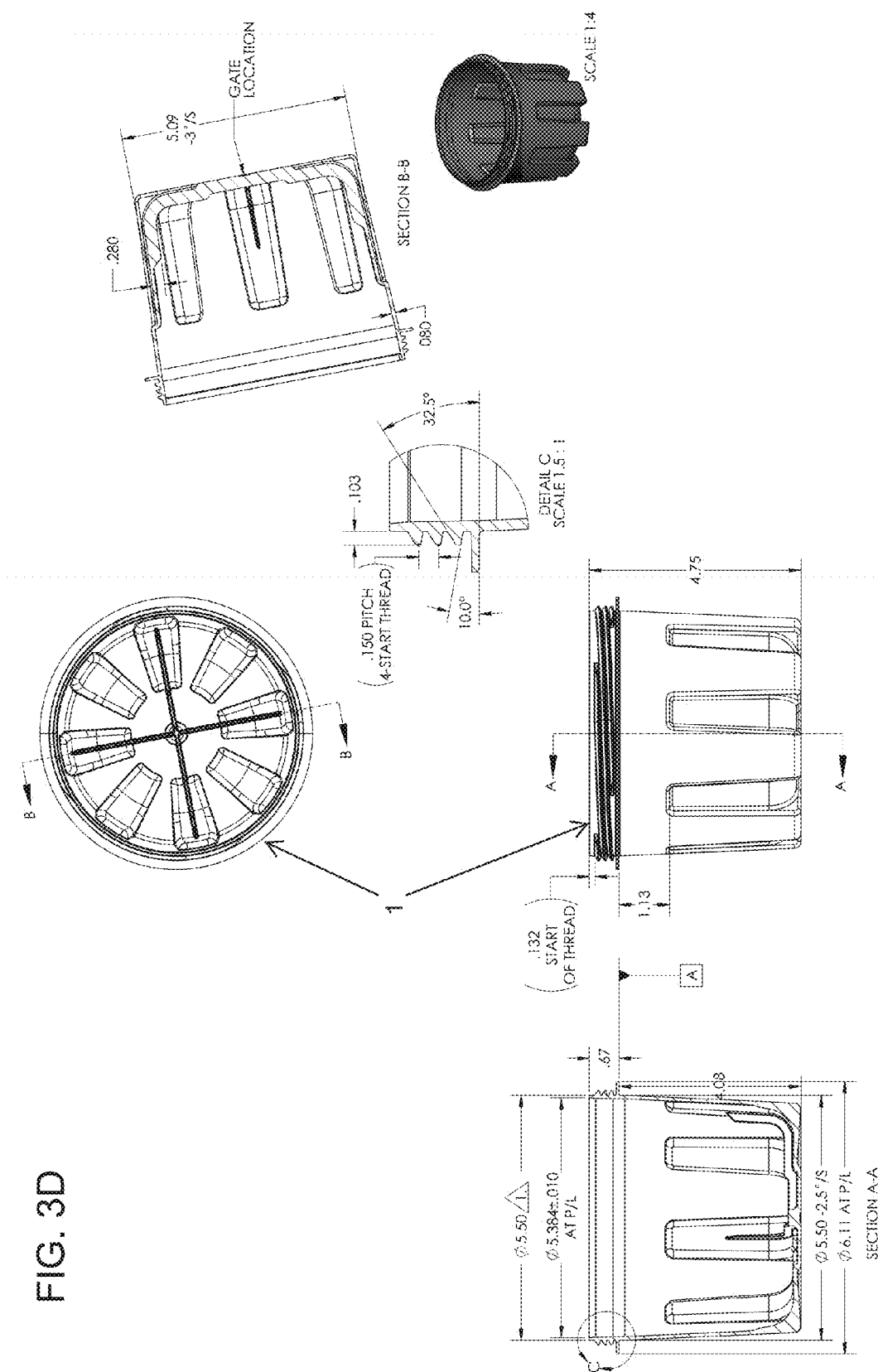

An exemplary embodiment of a sample container for use in the enclosing holder is shown in FIGS. 1 and 3A-D. The container shown comprises a bucket (1) and a lid (2), with a seal (3). As shown in FIG. 3D, the bucket (1) has a wide opening for receiving a stool sample. In the embodiment shown, the bucket is wider than it is tall, having a height of 4.75" and an outer diameter of 5.5" exclusive of the flange, (6.11" at the edge of the flange). The volume of the bucket is approximately 1400 mL (1.4 L).

The bucket (1) features a series of eight gripping ridges disposed around the circumference, starting about 1.13" below a flange and extending to the base of the bucket. The sides of the bucket (at the outermost dimensions that exclude the threads and flange) are essentially straight and slightly off of parallel, with the base outer diameter being slightly smaller than the outer diameter at the top edge (5.09" vs. 5.5").

Figure 5:
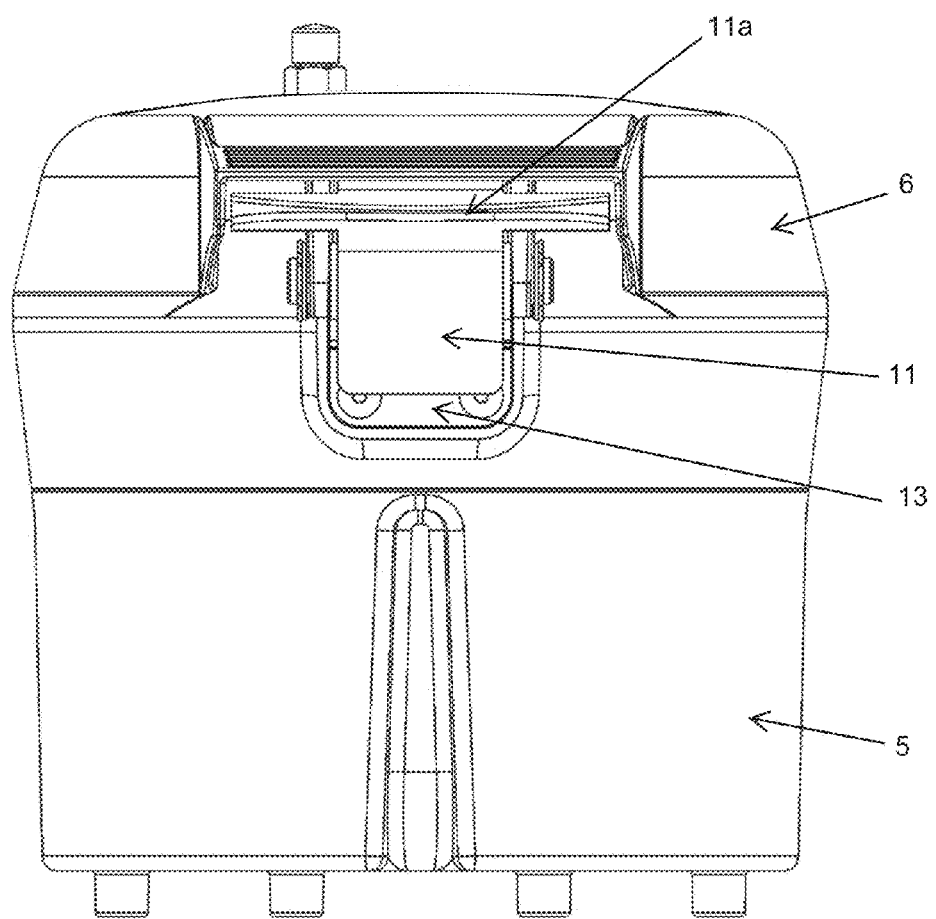

The interior of the bucket displays a series of protruding ridges that correspond to the grooves on the outside of the bucket (such as are shown in FIG. 2). Also as shown in FIG. 5, the interior side of the bucket comprises a smooth circumferential vertical surface immediately below the top edge.

As shown in FIG. 3A, the lid (2) has a cross-shaped handle gripping feature on its top, with four arms at right angles to each other and extending from a central circular hub to the edge of the lid. The height of the gripping feature from the surface of the lid is approximately 0.6" at the hub, with each arm tapering slightly downward in height toward the edge of the lid. The lid further comprises arrows and markings indicating the direction the lid is to be turned to engage or disengage the lid from the bucket. As shown, the lid is 5.75" in diameter; 6.125" to edge of flange on its bottom edge. The lid is 0.85" high to top of body of the lid and 1.45" high to top of handle.

FIG. 3B shows a floating plate seal for use with the lid of FIG. 3A and the bucket of FIG. 3D. The floating plate is 5.62" diameter to edge of plate and has a gasket seal of 5.393" diameter. The gasket seal has a "7" shape in cross-section, such that it can contact and seal against both the top edge and interior vertical surface of the bucket. The overall height of the floating plate with the gasket is approximately 0.5". FIG. 3C shows the lid and the floating plate seal separately, and as assembled into a lid assembly ready for use, with the floating plate inside the lid.

B. Enclosing Holder

Technology herein provides an enclosing holder that is directed toward both 1) reinforcing the integrity of the seal of a sample container during shaking, and 2) containing any sample leaking from the container such that, in the event of a leak, the mechanical shaker remains clean and usable, and contamination is contained within an article (the enclosing holder) that may be easily replaced with a clean enclosing holder, minimizing the effect of a leakage event on laboratory work-flow. Further, the contaminated enclosing holder is readily cleanable for future use.

In the embodiment shown, e.g., in FIGS. 4-19, hinges that are integrated with the top and base of the holder are stronger than, for example, hinges that are removably attached, e.g., by screws or bolts. In addition to being stronger and being simpler to manufacture, integrated hinges provide fewer seams, and are therefore easier to clean.

Use of integrated container-engaging features in the holder base (5) and/or holder top (6) avoids the need to use additional removable parts, e.g., plastic or metal adapters, which typically require adjustment, which are more readily damaged during use, and which are more difficult to clean.

In the embodiment shown, e.g., in FIGS. 4-14, the holder top (6) comprises an integrated handle (7) with ridges (7*a*) on the handle, e.g., to reduce slippage on the surface when the top is pressed to close the holder. The handle (7) of the top (6) is configured with a latch (11) that engages a catch (13) on the holder base when the top (6) is pressed to seat the top (6) on the base (5). The hinge of the enclosing holder is fitted with torsion springs (9) such that the top (6) will be held in an open position, and will pop open when latch (11) is not engaged to catch (13) on the base. Latch (11) comprises a latch release (11*a*) arranged on the underside of handle (7) such that an lifting or upward pressing motion on the underside of handle (7) will release the latch and allow the top (6) to move easily to a fully open position, propelled by the torque exerted by the torsion springs (9).

The enclosing holder is configured to be mounted securely, e.g., bolted or clamped, to a mechanical shaker. In preferred embodiments, the mechanical shaker comprises a cabinet enclosure closable around the mounted enclosing holder. In particularly preferred embodiments, when an enclosing holder is mounted in the mechanical shaker and is in an open configuration, the cabinet of the mechanical shaker cannot be closed, e.g., the top (6) of the enclosing holder, when in an open position, impedes a cabinet door or cover, such that the shaker cabinet cannot be closed and the shaker cannot be inadvertently operated when the enclosing holder within it is open.

C. Method of Processing a Stool Sample in a Buffer

The technology herein finds use in the processing of samples, e.g., human stool samples, in a buffer, e.g., a stabilizing buffer (see, e.g., U.S. Pat. Nos. 6,406,857 and 6,551,777; and Olson J, et al., Diagn Mol Pathol 14:183-91 (2005), each of which is incorporated herein by reference in its entirety).

1. In an ergonomic sample container as described in above in Example 1, part A, collect a sample of human stool, preferably having a mass of at least 4 grams;

2. To the stool sample in the sample container, add a stabilizing buffer, e.g., a Tris buffer comprising EDTA, in a volume of at least about 4 mL of buffer per gram of stool sample.

3. Seal the sample container by engaging the lid to the bucket, e.g., by engaging the threaded engagement portion of the bucket with a mated threaded portion of the lid, with a seal disposed therebetween to provide a sealed container containing the stool sample and buffer;

4. Place the sealed sample container in a sample mixer (e.g., a mechanical shaker) that comprises an enclosing holder as described above in Example 1, part B. Close the enclosing holder such that the latch (11) engages the catch (13). For an enclosing holder as shown in FIGS. 4-14, the enclosing holder is closed and the latch and catch are engaged by swinging the top (6) down over the top of the sample container and pressing the top (6), e.g., at handle (7), until latch (11) engages the catch (13).

5. Close the sample mixer cabinet;

6. Operate the sample mixer for a period of time during which the stool sample and buffer are homogenized.

7. Open the sample mixer cabinet;

8. Open the enclosing holder. For an enclosing holder as shown in FIGS. 4-14, the latch and catch are disengaged by lifting up on the latch release (11*a*) on the underside of handle (7), such that the latch and catch are disengaged and the top (6) of the enclosing holder swings open by force of the torsion springs (9), an operation typically accomplished using one hand.

9. Remove the sealed sample container containing the homogenized stool sample from the base of the enclosing holder.

The homogenized stool sample may then be analyzed, e.g., as described in WO 2012/155072, which is incorporated herein by reference in its entirety.

Although the disclosure herein refers to certain illustrated embodiments, it is to be understood that these embodiments are presented by way of example and not by way of limitation. All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in engineering, material science, pharmacology, biochemistry, medical science, or related fields are intended to be within the scope of the following claims.

I claim:

1. An enclosing holder for a sealed sample container, said enclosing holder comprising:
   a) a holder base comprising a body having a base bottom wall joined around a circumference to a bottom edge of a base side wall, a top edge of the base side wall circumferentially defining a top opening of the base, the base bottom wall and the top opening of the base defining therebetween a vertical direction on the base of the enclosing holder, wherein an interior side of the base side wall defines a circumferential vertical surface between the bottom wall and the top opening of the body of the holder base, the holder base further comprising:
      i) a first latching engagement feature removeably engageable with a mated latching feature on a holder top;
      ii) a first integrated hinge portion; and
      iii) a first sample container-engaging feature comprising a plurality of integral vertical ridges on the circumferential vertical surface of the base side wall;
   b) a holder top comprising a body comprising an interior side that is disposed toward the interior of the holder base when the enclosing holder is in a closed configuration, and an exterior, said holder top further comprising:
      i) the mated latching engagement feature, removeably engageable with the first latching engagement feature on the holder base;
      ii) a second integrated hinge portion, flexibly engaged with the first integrated hinge portion of the holder base;
      iii) a second sample container-engaging feature comprising at least one ridge integrally formed on the interior side of the holder top; and
      iv) a handle;
   c) a spring configured to move the holder top of said enclosing holder to an open position when said first latching engagement feature and said mated latching engagement feature are disengaged;
   d) a latch release reversibly movable from a first position to a second position, wherein in said second position, said first latching engagement feature is disengaged from said mated latching engagement feature;
   e) a valve; and
   d) at least one threaded hole for mounting the enclosing holder in a mechanical shaker with a screw and/or bolt;
   wherein when said first latching engagement feature is engaged to said second latching engagement feature, said enclosing holder is in a closed configuration forming an airtight enclosed space in the interior of said body of the enclosing holder that is isolated from the exterior of said body of the enclosing holder, said valve providing a valved connection between said enclosed space and the exterior of enclosing holder.

2. The enclosing holder of claim 1, wherein said bodies of said holder base and/or said holder top are composed of metal.

3. The enclosing holder of claim 2, wherein said metal is aluminum.

4. The enclosing holder of claim 1, wherein said handle is an integrated handle with respect to the body of the holder top.

5. The enclosing holder of claim 1, wherein the spring comprises a torsion spring.

6. A system for shaking homogenization of a sample, the system comprising a sample container and an enclosing holder for the sample container, wherein:
   i) the sample container comprises:
      a) a bucket having an internal volume of at least 300 ml, the bucket comprising:
         I) a bucket bottom wall joined around a circumference to a bottom edge of a bucket side wall, a top edge of the bucket side wall circumferentially defining a top opening of the bucket, wherein the bucket bottom wall and the top opening of the bucket define therebetween a vertical direction on the bucket side wall, and wherein an exterior surface of the bucket side wall defines an exterior circumferential surface of the bucket,
         II) a plurality of ridges on the exterior circumferential surface, the ridges distributed radially with respect to a bucket central axis; and
         III) a first threaded engagement portion; and
      b) a lid having a lid central axis, the lid comprising:
         I) a lid top wall joined around a circumference to a top edge of a lid side wall, a bottom edge of the lid side wall defining a bottom opening of the lid, the lid top wall comprising an interior surface disposed to the bottom opening of the lid, and an exterior surface comprising at least one raised ridge;
         II) a mated threaded engagement portion removeably engageable with the first threaded engagement portion of the bucket;
         wherein, when threads of the first threaded engagement feature of the bucket and of the mated threaded engagement feature of the lid are engaged with each other, said bucket central axis and the lid central axis are collinear, and a junction between the lid and the bucket is sealed to form a sealed sample container;
   ii) the enclosing holder comprises:
      a) a holder base comprising a body having a base bottom wall joined around a circumference to a bottom edge of a base side wall, a top edge of the base side wall circumferentially defining a top opening of the base, the base bottom wall and the top opening of the base defining therebetween a vertical direction on the base of the enclosing holder, wherein an interior side of the base side wall defines a circumferential vertical surface between the bottom wall and the top opening of the body of holder base, the base further comprising:
         I) a first latching engagement feature removeably engageable with a mated latching feature on a holder top;
         II) a first integrated hinge portion; and
         III) a first sample container-engaging feature comprising a plurality of integral vertical ridges on the circumferential vertical surface of the base side wall engageable with at least one vertical ridge on the sample container bucket;
      b) a holder top comprising an interior side that is disposed toward the interior of the holder base when the enclosing holder is in a closed configuration, and an exterior, the holder top further comprising:
         I) the mated latching engagement feature, removeably engageable with the first latching engagement feature on the holder base;

II) a second integrated hinge portion, flexibly engaged with the first integrated hinge portion of the holder base;

III) a second sample container-engaging feature comprising at least one ridge integrally formed on the interior side of the holder top, engageable with the at least one raised ridge on the sample container lid; and IV) a handle;

c) a spring configured to move the holder top of the enclosing holder to an open position when the first latching engagement feature and the mated latching engagement feature are disengaged;

d) a latch release reversibly movable from a first position to a second position, wherein in the second position, the first latching engagement feature is disengaged from said mated latching engagement feature;

e) a valve;

f) at least one threaded hole for mounting the enclosing holder in a mechanical shaker with a screw and/or bolt;

wherein when the first latching engagement feature is engaged to the second latching engagement feature, the enclosing holder is in a closed configuration forming an airtight enclosed space in the interior of said body of the enclosing holder that is isolated from the exterior of the body of the enclosing holder, the valve providing a valved connection between the enclosed space and the exterior of enclosing holder; and wherein, when a sealed sample container is enclosed the enclosing holder in the closed configuration, the lid of the sample container is constrained from rotating with respect to the bucket of the sample container, around the lid central axis.

7. The system of claim 6, wherein the bodies of the holder base and/or the holder top are composed of metal.

8. The system of claim 7, wherein said metal is aluminum.

9. The system of claim 6, wherein said handle is an integrated handle with respect to the body of the holder top.

10. The system of claim 6, wherein the spring comprises a torsion spring.

11. The system of claim 6, wherein the hole is an exterior hole in the base bottom wall of the holder base.

12. The system of claim 6, wherein the hole is a is a threaded hole engageable with a screw.

13. The system of claim 6, wherein the valve is a Schrader valve.

14. The system of claim 6, further comprising a stool homogenization solution.

15. The system of claim 14, wherein said stool homogenization solution comprises a salt and a preservative or a stabilizing agent.

* * * * *